(12) United States Patent
Hanson et al.

(10) Patent No.: US 10,569,014 B2
(45) Date of Patent: Feb. 25, 2020

(54) DEVICE AND METHOD FOR MAKING ASEPTIC CONNECTIONS

(71) Applicant: AMGEN INC., Thousand Oaks, CA (US)

(72) Inventors: Ian B. Hanson, Wayne, PA (US); Lawton Laurence, Phoenixville, PA (US); Antonio Ubach, Tucson, AZ (US); Rajan Ramaswamy, San Diego, CA (US); Daniel S. Codd, Escondido, CA (US); Scott Beaver, San Marcos, CA (US); Kevin L. Bokelman, San Diego, CA (US); Danielle Feldman, Philadelphia, PA (US); Matthew J. Clemente, Carmel, IN (US)

(73) Assignee: AMGEN INC., Thousand Oaks, CA (US)

(*) Notice: Subject to any disclaimer, the term of this patent is extended or adjusted under 35 U.S.C. 154(b) by 192 days.

(21) Appl. No.: 15/552,828

(22) PCT Filed: Mar. 2, 2016

(86) PCT No.: PCT/US2016/020486
§ 371 (c)(1),
(2) Date: Aug. 23, 2017

(87) PCT Pub. No.: WO2016/141082
PCT Pub. Date: Sep. 9, 2016

(65) Prior Publication Data
US 2018/0028747 A1    Feb. 1, 2018

Related U.S. Application Data

(60) Provisional application No. 62/148,082, filed on Apr. 15, 2015, provisional application No. 62/127,021, filed on Mar. 2, 2015.

(51) Int. Cl.
*A61M 5/162* (2006.01)
*A61M 5/158* (2006.01)
(Continued)

(52) U.S. Cl.
CPC ............ *A61M 5/162* (2013.01); *A61M 5/142* (2013.01); *A61M 5/1413* (2013.01);
(Continued)

(58) Field of Classification Search
CPC ........ A61J 1/1406; A61J 1/201; A61J 1/2051; A61M 2005/14252; A61M 2005/1585;
(Continued)

(56) References Cited

U.S. PATENT DOCUMENTS 6,022,339 A    2/2000 Fowles et al.
2011/0166512 A1* 7/2011 Both ................. A61M 5/14248
604/67

(Continued)

FOREIGN PATENT DOCUMENTS

WO    WO-2010/029054 A1    3/2010
WO    WO-2013/033421 A2    3/2013
(Continued)

OTHER PUBLICATIONS

International Search Report and Written Opinion issued in International Application No. PCT/US2016/020486, dated Jun. 20, 2016.
(Continued)

*Primary Examiner* — Imani N Hayman
(74) *Attorney, Agent, or Firm* — Marshall, Gerstein & Borun LLP

(57) ABSTRACT

The present invention provides devices and methods for establishing aseptic connections between two or more components or subassemblies. The devices may be used in medical devices such as drug delivery pumps (10). In some embodiments, a connection is made between a drug con-
(Continued)

tainer (50, 1050, 2050) and a fluid pathway connection assembly (300, 1300, 2300). The fluid pathway connection assembly may include a connection hub (312, 1312, 2312), a piercing member (316, 1316, 2316), and a piercing member retainer (314, 1314, 2314). The assembly may further include a first film (318, 1318, 2318) covering a cavity (312A, 1312A, 2312A), thereby maintaining the aseptic condition of the cavity. The drug container may hold a fluid drug and include a pierceable seal (326, 1326, 2326). A second film (322, 1322, 2322) may cover a recess (328, 1328, 2328) formed by the seal and thereby maintain the aseptic condition of the interior of the chamber. The piercing member may be caused to pierce the first and second film and the pierceable seal to open a fluid pathway for delivery of the fluid drug through the fluid pathway connection assembly.

20 Claims, 25 Drawing Sheets

(51) Int. Cl.
  *A61M 5/14* (2006.01)
  *A61M 5/142* (2006.01)
(52) U.S. Cl.
  CPC .......... *A61M 5/158* (2013.01); *A61M 5/1626* (2013.01); *A61M 2005/1585* (2013.01); *A61M 2205/0216* (2013.01); *A61M 2205/18* (2013.01); *A61M 2205/581* (2013.01); *A61M 2205/587* (2013.01)

(58) Field of Classification Search
  CPC .... A61M 2005/2474; A61M 2005/341; A61M 2205/0216; A61M 2205/18; A61M 2205/581; A61M 2205/587; A61M 39/18; A61M 5/1413; A61M 5/142; A61M 5/14248; A61M 5/1456; A61M 5/158; A61M 5/162; A61M 5/1626; A61M 5/32
  See application file for complete search history.

(56) References Cited

U.S. PATENT DOCUMENTS

2013/0066274 A1  3/2013  O'Connor et al.
2014/0200510 A1  7/2014  Agard et al.

FOREIGN PATENT DOCUMENTS

WO  WO-2013/033467 A2  3/2013
WO  WO-2014/036239 A2  3/2014
WO  WO-2016/053954 A1  4/2016

OTHER PUBLICATIONS

International Search Report and Written Opinion, International Application No. PCT/US2016/020486, dated Sep. 5, 2017.
International Preliminary Report on Patentability issued in International Patent Application No. PCT/US2016/020486, dated Sep. 5, 2017.

* cited by examiner

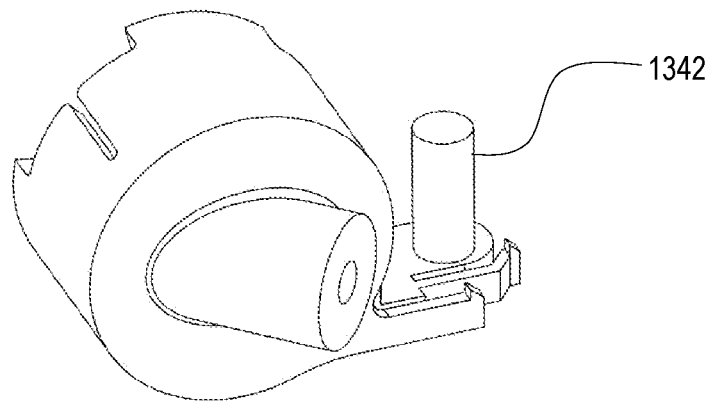
FIG. 19
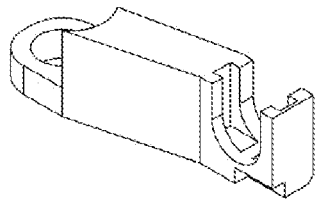
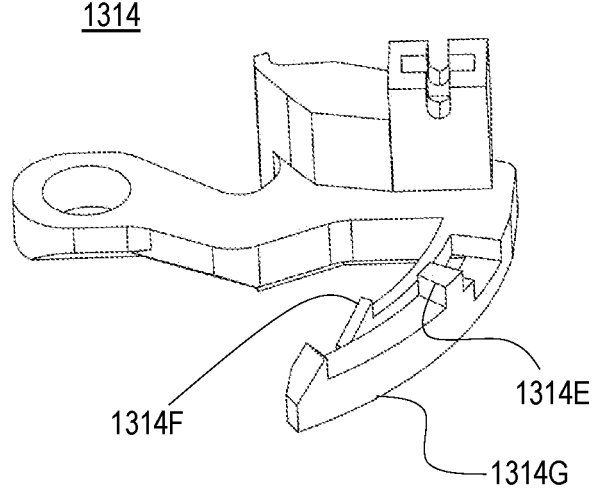
FIG. 20                FIG. 21

DEVICE AND METHOD FOR MAKING ASEPTIC CONNECTIONS

CROSS-REFERENCE TO RELATED APPLICATIONS

This application is a United States national stage application of International Application No. PCT/US2016/020486, having an international filing date of Mar. 2, 2016, which claims priority to U.S. Provisional Application No. 62/127,021, filed on Mar. 2, 2015 and to U.S. Provisional Application No. 62/148,082, filed on Apr. 15, 2015, all of which are included by reference herein in their entireties for all purposes.

FIELD

This invention relates to aseptic connections. More particularly, this invention relates to devices and methods for making aseptic connections in septic environments, thereby allowing components to be integrated into drug delivery devices.

BACKGROUND

Parenteral delivery of various drugs, i.e., delivery by means other than through the digestive track, has become a desired method of drug delivery for a number of reasons. This form of drug delivery by injection may enhance the effect of the substance being delivered and ensure that the unaltered medicine reaches its intended site at a significant concentration. Similarly, undesired side effects associated with other routes of delivery, such as systemic toxicity, can potentially be avoided through parenteral delivery. By bypassing the digestive system of a mammalian patient, one can avoid degradation of the active ingredients caused by the catalytic enzymes in the digestive tract and liver and ensure that a necessary amount of drug, at a desired concentration, reaches the targeted site.

Traditionally, manually operated syringes and injection pens have been employed for delivering parenteral drugs to a patient. More recently, parenteral delivery of liquid medicines into the body has been accomplished by administering bolus injections using a needle and reservoir, continuously by gravity driven dispensers, or via transdermal patch technologies. Bolus injections can imperfectly match the clinical needs of the patient, and may require larger individual doses than are desired at the specific time they are given. Continuous delivery of medicine through gravity-feed systems compromises the patient's mobility and lifestyle, and limits the therapy to simplistic flow rates and profiles. Another form of drug delivery, transdermal patches, similarly has its restrictions. Transdermal patches often require specific molecular drug structures for efficacy, and the control of the drug administration through a transdermal patch is severely limited.

Ambulatory infusion pumps have been developed for delivering liquid medicaments to a patient. These infusion devices have the ability to offer sophisticated fluid delivery profiles accomplishing bolus requirements, continuous infusion and variable rate delivery. These infusion capabilities usually result in better efficacy of the drug and therapy and less toxicity to the patient's system. Currently available ambulatory infusion devices are expensive, difficult to program and prepare for infusion, and tend to be bulky, heavy and very fragile. Filling these devices can be difficult and require the patient to carry both the intended medication as well as filling accessories. The devices often require specialized care, maintenance, and cleaning to assure proper functionality and safety for their intended long-term use, and are not cost-effective for patients and healthcare providers.

As compared to syringes and injection pens, pump type delivery devices can be significantly more convenient to a patient, in that doses of the drug may be calculated and delivered automatically to a patient at any time during the day or night. Furthermore, when used in conjunction with metabolic sensors or monitors, pumps may be automatically controlled to provide appropriate doses of a fluidic medium at appropriate times of need, based on sensed or monitored metabolic levels. As a result, pump type delivery devices have become an important aspect of modern medical treatments of various types of medical conditions, such as diabetes, and the like.

While pump type delivery systems have been utilized to solve a number of patient needs, manually operated syringes and injection pens often remain a preferred choice for drug delivery as they now provide integrated safety features and can easily be read to identify the status of drug delivery and the end of dose dispensing. However, manually operated syringes and injection pens are not universally applicable and are not preferred for delivery of all drugs. There remains a need for an adjustable (and/or programmable) infusion system that is precise and reliable and can offer clinicians and patients a small, low cost, light weight, simple to use alternative for parenteral delivery of liquid medicines.

There is a strong market demand for drug delivery devices which are easy-to-use, cost-efficient, and which include integrated safety features. However, manufacturing of such devices can be cost intensive, which results in higher costs to patients. Much of the manufacturing costs can be attributed to the need to maintain a sterile fluid pathway from the drug container to the needle, prior to introduction of the drug to the patient. Some commercial products seek to maintain the sterility of the device by manufacturing the components in a non-sterile environment and then sterilizing the entire device. A recognized downside of such processes is the need to separately fill the drug container after the device sterilization, but prior to drug injection, as most pharmaceutical compounds are not capable of withstanding the device sterilization process. Alternatively, the drug delivery device may be manufactured as a pre-filled device, wherein the device is filled with the drug aseptically during assembly. Such manufacturing processes may be costly since the entire process must be kept sterile and because the fill and assembly lines need to be specially-tailored for the device. Accordingly, this adds substantial operating costs to pharmaceutical companies and contract drug-fillers.

Drug delivery devices are generally prepared by molding or shaping the various components and then assembling the components. The assembling steps and other processing operations typically produce a device that subsequently must be cleaned to remove particulates adhering to the surfaces to satisfy cleanliness standards for drug delivery devices. After cleaning, conventional drug delivery devices are packaged and sterilized. Such delivery devices have been classified into several general types. The first type is assembled and placed in sterile packaging which can be shipped with a vial or ampoule of a drug or other injectable solution. The vial or ampoule is generally made of glass or other clear material that does not interfere with the stability of the drug during prolonged storage. The delivery device is filled with the drug or other solution at the point of use and injected into the patient. These devices have the disadvantage of increasing the time and difficulty of filling the device at the point of use with increased possibility of contamination of the delivery device and/or drug solution. There is a further risk of glass particles from the ampoules contaminating the drug solution when the ampoules are opened.

Several of these disadvantages are overcome by providing prefilled delivery devices which can be filled with a suitable drug solution prior to use. Prefilled delivery devices, as the term is known in the art, are devices that are filled by the drug manufacturer and shipped to the health care provider or self-administering patient in a condition that is ready for use. Prefilled delivery devices have the advantage of convenience and ease of application with reduced risk of contamination of the drug solution. Prefilled drug delivery devices are generally assembled and packaged in clean rooms to maintain proper cleanliness levels. The clean rooms are equipped with extensive filter assemblies and air control systems to remove particulates and pyrogens from the air in the room and to prevent particulates and pyrogens from entering the room. The operators and other personnel in the clean room are required to wear appropriate protective garments to reduce contamination of the air and the drug delivery devices being manufactured or assembled. As people and equipment enter and leave the clean room, the risk of contamination and introduction of foreign particulates and pyrogens increases. Various operations are able to form clean and sterile drug delivery devices. However, subsequent handling, filling and printing of the drug delivery device can contaminate the device. It is then necessary to clean and sterilize such conventional drug delivery devices before use. Accordingly, there is a continuing need in the industry for an improved system for manufacturing and assembling clean and sterile medical devices and filling such devices.

SUMMARY

The present invention provides devices and methods for establishing aseptic connections between two or more components or subassemblies. The devices may be used in medical devices such as drug delivery pumps. In some embodiments, a connection is made between a drug container and a fluid pathway connection assembly. The fluid pathway connection assembly may include a connection hub, a piercing member, and a piercing member retainer. The mechanism may further include a first film or seal covering an aperture, thereby maintaining the aseptic condition of a cavity adjacent the aperture. The drug container may hold a fluid drug and include a pierceable seal. A second film may cover an aperture of one or more components of the drug container and the seal, and thereby maintain the aseptic condition of the pierceable seal. The piercing member may be caused to pierce the first and second film and the pierceable seal to open a fluid pathway for delivery of the fluid drug to a patient.

In a first embodiment, the present invention provides a fluid pathway connection. The fluid pathway connection assembly includes: a connection hub, a piercing member, a piercing member retainer, and a drug container having a cap, a pierceable seal, and a barrel, wherein the piercing member is at least partially disposed in a sterile cavity defined by the connection hub. The drug container may contain a drug fluid for delivery through the fluid pathway connection assembly to the target. The pierceable seal includes a seal barrier that may be penetrated by the piercing member. The fluid pathway connection assembly may further include a first film which is fixedly attached over an aperture over an aperture of the connection hub and prevents foreign substances such as microbes from entering the sterile cavity formed by the connection hub. The drug container may further include a second film fixedly connected over a cavity formed by the pierceable seal and the second film to prevent foreign substances such as microbes from entering the cavity. The first and second films may be pierced by the piercing member. The fluid pathway connection may be initiated directly by the user, or may be activated by another mechanism of the device (as described herein) after some initial user step.

In another embodiment, the present invention provides a drug delivery pump with integrated sterility maintenance features having a housing and an assembly platform, upon which an activation mechanism, a fluid pathway connection assembly, a power and control system, and a drive mechanism having a drug container may be mounted, said fluid pathway connection assembly including a connection hub, a piercing member, a piercing member retainer, and a drug container having a cap, a pierceable seal, and a barrel, wherein the piercing member is at least partially disposed in a sterile cavity defined by the connection hub. The drug container may contain a drug fluid for delivery through the fluid pathway connection assembly to the target. The pierceable seal includes a seal barrier that may be penetrated by the piercing member. The fluid pathway connection assembly may further include a first film which is fixedly attached over an aperture over an aperture of the connection hub and prevents foreign substances such as microbes from entering the sterile cavity formed by the connection hub. The fluid pathway connection assembly may further include a second film fixedly connected over a cavity formed by the pierceable seal and prevents foreign substances such as microbes from entering the cavity. The first and second films may be pierced by the piercing member.

The devices described herein may further include features which prevent the delivery of an excess volume of medicament or delivery at too rapid of a rate, e.g., to prevent a run-away condition of uncontrolled or undesired delivery of the medicament. By providing such automatic safety mechanisms, the safety of the patient may be ensured. Some medicaments, such as insulin or other treatments for diabetes, can be dangerous, and potentially even deadly, if they are not delivered according to prescribed parameters. The safety features described below may ensure that delivery of the medicament is terminated if delivery deviates from the specified parameters.

In a further embodiment of the present invention, the fluid pathway connection assembly may include one or more biasing members. In one such embodiment, a biasing member may be included to bias the fluid pathway connection assembly to connect, i.e., to open the fluid pathway between the drug container and the fluid conduit which enables drug flow to the needle insertion mechanism and into the target. In such a configuration, the fluid pathway connection assembly is biased to facilitate the connection upon, for example, movement of a pin or blocking aspect. In at least one embodiment, the biasing member(s) may be internal to the fluid pathway connection assembly and/or external to the fluid pathway connection assembly to facilitate the connection once triggered. Additionally or alternatively, one or more biasing members may be included to disconnect the fluid pathway connection assembly. This may provide a desirable safety feature, to disconnect the fluid pathway upon signaling of an error condition either automatically by the drug delivery pump or upon action by the user. Once the fluid pathway connection assembly is disconnected, flow of drug fluid is restricted or blocked between the drug container and the fluid conduit to limit or prevent fluid flow to the needle insertion mechanism and into the target.

According to an aspect of the disclosure, there is provided a fluid pathway connection assembly for use with a drug container in a drug delivery pump. The drug container includes a barrel, a cap and a pierceable seal. The fluid pathway connection assembly includes an unactuated configuration, an actuated configuration, and a delivery configuration. The fluid pathway connection assembly includes a connection hub including an aperture, a first film, an introducer member, a piercing member, and a piercing member retainer. The first film is sealed along the aperture. The connection hub includes a sterile cavity sealed by the first film. The introducer member is at least partially disposed within the sterile cavity in the unactuated configuration. The piercing member is configured to telescope from the introducer member. The piercing member includes a piercing tip at least partially disposed within the introducer member in the unactuated configuration. The piercing member retainer is connected to the piercing member. The introducer member is configured to move relative to the connection hub from the unactuated configuration to the actuated configuration in which the introducer member pierces the first film. The piercing member is configured to telescope from the introducer member to move from the unactuated configuration to the delivery configuration in which the piercing tip is not disposed within the introducer member. The piercing member is adapted to pierce the pierceable seal in the delivery configuration, the piercing member providing a fluid pathway through the piercing member connection hub in the delivery configuration. In at least one embodiment, there is provided a combination of the fluid pathway connection assembly and the drug container. In at least one embodiment, there is provided a drug delivery pump including a housing, an activation mechanism, the fluid pathway connection assembly, and a drug container.

In at least one embodiment, the fluid pathway connection assembly is configured to move the piercing member from the delivery configuration to a retracted configuration wherein the piercing member is disengaged from the pierceable seal in response to a termination mechanism.

The novel embodiments of the present invention provide fluid pathway connections to drug containers, and drug pumps which utilize such connections which are capable of maintaining the sterility of the fluid pathway before, during, and after operation of the device, and which enable active safety controls for the device. Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present invention may include one or more additional components which may be considered standard components in the industry of medical devices. The components, and the embodiments containing such components, are within the contemplation of the present invention and are to be understood as falling within the breadth and scope of the present invention.

BRIEF DESCRIPTION OF DRAWINGS

The following non-limiting embodiments of the invention are described herein with reference to the following drawings, wherein:

FIG. 19 shows an isometric view of a connection hub according to at least one embodiment of the present invention;

FIG. 20 shows an isometric view of an embodiment of an introducer member retainer according to at least one embodiment of the present invention;

FIG. 21 shows an isometric view of an embodiment of a piercing member retainer according to at least one embodiment of the present invention;

DETAILED DESCRIPTION

Figure 1A:
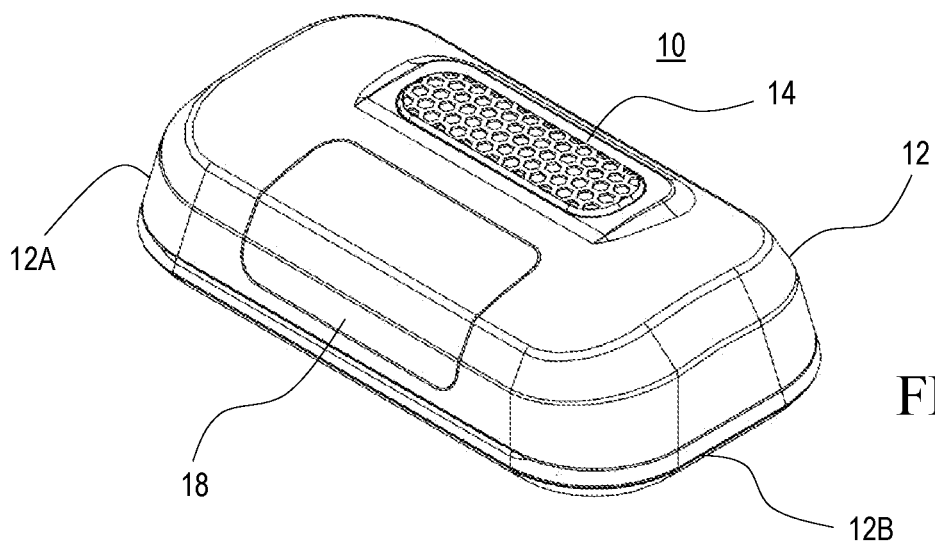
FIG. 1A is an isometric view of an embodiment of a drug delivery pump.

As used herein to describe the drive mechanisms, drug delivery pumps, or any of the relative positions of the components of the present invention, the terms "axial" or "axially" refer generally to a longitudinal axis "A" around which the drive mechanisms are preferably positioned, although not necessarily symmetrically there-around. The term "radial" refers generally to a direction normal to axis A. The terms "proximal," "rear," "rearward," "back," or "backward" refer generally to an axial direction in the direction "P". The terms "distal," "front," "frontward," "depressed," or "forward" refer generally to an axial direction in the direction "D". As used herein, the term "glass" should be understood to include other similarly non-reactive materials suitable for use in a pharmaceutical grade application that would normally require glass, including but not limited to certain non-reactive polymers such as cyclic olefin copolymers (COC) and cyclic olefin polymers (COP). The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration under ambient temperature and pressure. "Fluid" refers primarily to liquids, but can also include suspensions of solids dispersed in liquids, and gasses dissolved in or otherwise present together within liquids inside the fluid-containing portions of the pumps. According to various aspects and embodiments described herein, reference is made to a "biasing member", which may be any member that is capable of storing and releasing energy. Non-limiting examples include a spring, such as for example a coiled spring, a compression or extension spring, a torsional spring, and a leaf spring, a resiliently compressible or elastic band, or any other member with similar functions. In at least one embodiment of the present invention, the biasing member is a spring.

The novel devices of the present invention provide container connections which maintain the sterility and/or aseptic condition of the fluid pathway, and drug delivery pumps which incorporate such sterile fluid pathway connection assemblies to drug containers. Such devices are safe and easy to use, and are aesthetically and ergonomically appealing for self-administering patients. The fluid pathway connection may be initiated directly by the user, or may be activated by another mechanism of the device (as described herein) after some initial user step. The devices described herein incorporate features which make activation, operation, and lock-out of the device simple for even untrained users. The novel devices of the present invention provide these desirable features without problems associated with known prior art devices. Certain non-limiting embodiments of the novel drug delivery pumps, fluid pathway connection assemblies, and their respective components are described further herein with reference to the accompanying figures.

Conventional drug delivery devices often require filling at time-of-use because the terminal sterilization of the device cannot be completed with the pharmaceutical drug within the drug container. Various pharmaceutical drugs cannot withstand the temperatures, pressures, and other conditions necessary for sterilization of the device after assembly. In other words, because existing manufacturing processes require sterilization of the entire device, the drug cannot be "pre-filled" into the device prior to sterilization. This adds a complex step after final assembly of the device, which often requires costly additional equipment, handling of separate drug containers, and/or training of the patient to perform the filling step themselves prior to injection. Instead, the embodiments of the present invention enable the manufacture, assembly, and use of pre-filled drug delivery devices which maintain the sterility and/or aseptic condition of the fluid pathway assembly through the various manufacturing steps.

Additionally, because the drug delivery devices which incorporate the novel embodiments of the present invention do not need to be terminally sterilized, the components of the devices may be constructed of other, often less expensive, materials which would not normally withstand the sterilization environment. For example, less expensive plastics may be utilized for certain device components because they do not need to be sterilized after assembly. Furthermore, the embodiments of the present invention permit device architecture and/or component integration in ways which are not suitable for devices that require terminal sterilization. For example, when sterilization of the entire device is necessary, the device architecture often requires adequate spacing of components to permit the sterilization gas or material to effectively reach the target surfaces. Removing the need for terminal sterilization permits reduction or elimination of those spaces and allows for device architectures that offer smaller overall dimensions, human factors benefits, and/or industrial design options that are not available for devices that require terminal sterilization.

In other words, the embodiments of the present invention may allow the manufacturer to sterilize only the components which will be in contact with the drug fluid and/or which are necessary to maintain sterile and/or aseptic fluid pathways. These embodiments may also allow the pharmaceutical filler to maintain the sterility and/or aseptic condition of these components during the filling and finishing steps associated with the assembly of the drug delivery devices. Similarly, drug delivery devices which incorporate the fluid pathway connection assemblies of the present invention may have smaller or more efficient geometries as the device does not have to be configured for sterilization after assembly.

Additionally, the embodiments of the present invention allow for the utilization of standard fill-finish processes to fill the drug container. This greatly simplifies the manufacturing processes used to build drug delivery devices. Standard fill-finish processes utilize trays which hold multiple drug containers, such as syringes. The embodiments of the present invention enable a drug delivery device manufacturer, pharmaceutical company, or contract drug filler to fill the drug containers for infusion or injection pumps using the same standard fill-finish processes. These drug containers can be filled aseptically, as is common industry practice, in a cost-efficient manner. After mounting of the fluid pathway connection assembly the combined assembly can then be mated into a drug delivery device without requiring the remainder of the device components to be sterilized. Accordingly, embodiments of the present invention may provide novel components which enable the fluid pathway assemblies to be sterilized, assembled, filled, and incorporated into drug delivery devices in a cost-efficient and streamlined process.

In the processes of filling drug containers and other drug delivery devices, it is sometimes necessary to connect two or more sterile components or subassemblies. For example, wearable injectors or drug pumps may include a drug container which may be filled with a fluid drug using standard pharmaceutical fill-finish processes. After filling of the drug container, it may be necessary to connect the drug container to one or more additional components or subassemblies such that a fluid communication may be established between the drug container and these components. Maintaining the fluid path in an aseptic condition is critical, preventing the introduction of harmful microbes or particulates to the drug and/or fluid pathway. The connection of two or more aseptic components or subassemblies is typically performed in an aseptic environment, such as a clean room, thereby ensuring that no harmful microbes or particulates are introduced to the assembly. This, however, may lead to increased cost to manufacture the drug delivery devices.

The novel devices of the present invention provide fluid pathway connection assemblies with integrated safety features and drug delivery pumps which incorporate such fluid pathway connection assemblies. Such devices are safe and easy to use, and are aesthetically and ergonomically appealing for self-administering patients. The devices described herein incorporate features which make activation, operation, and lock-out of the device simple for even untrained users. The novel devices of the present invention provide these desirable features without any of the problems associated with known prior art devices. Certain non-limiting embodiments of the novel drug delivery pump, fluid pathway connection assemblies, and their respective components are described further herein with reference to the accompanying figures. The devices described herein may be configured for delivery of controlled substances and may further include features that prevent so-called "run-away" delivery of medicament. When delivering controlled substances, this may be an important safety feature to protect the patient. For example, some medicaments, such as insulin, can be dangerous, and potentially even deadly, when administered in too large a quantity and/or at too rapid of a rate. By providing such automatic safety stop mechanisms, the safety of the patient may be ensured.

Figure 1B:
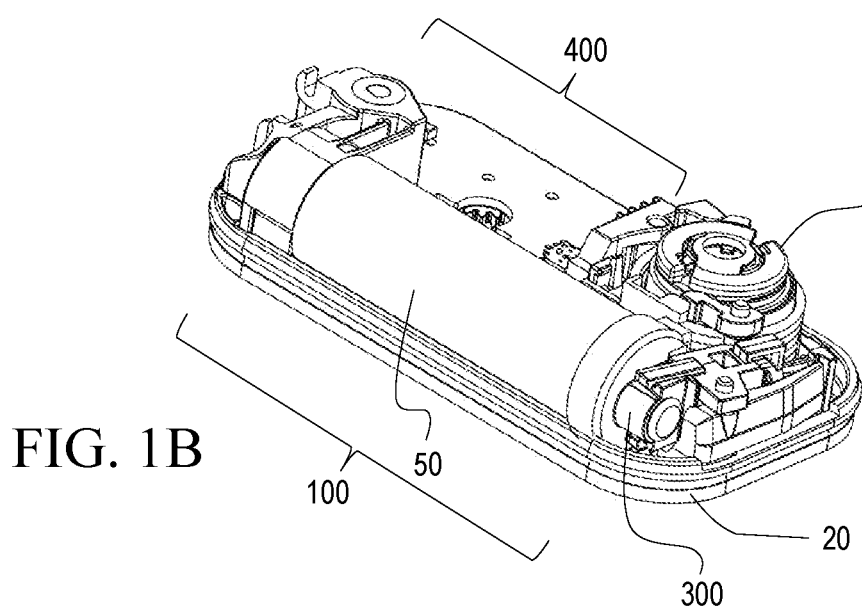
FIG. 1B shows an isometric view of the interior components of the drug delivery pump shown in FIG. 1A.
Figure 1C:
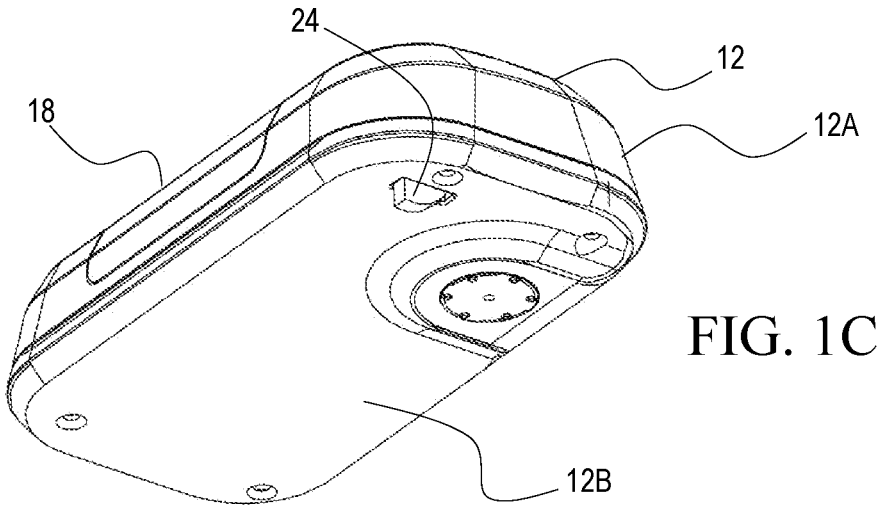
FIG. 1C shows an isometric view of the bottom of the drug delivery pump shown in FIG. 1A.

As used herein, the term "pump" is intended to include any number of drug delivery systems which are capable of dispensing a fluid to a target upon activation. Such drug delivery systems include, for example, injection systems, infusion pumps, bolus injectors, and the like. FIGS. 1A-1C show an exemplary drug delivery device according to at least one embodiment of the present invention. The drug delivery device may be utilized to administer delivery of a drug treatment into a target. As shown in FIGS. 1A-1C, the drug pump 10 includes a pump housing 12. Pump housing 12 may include one or more housing subcomponents which are fixedly engageable to facilitate easier manufacturing, assembly, and operation of the drug pump. For example, drug pump 10 includes a pump housing 12 which includes an upper housing 12A and a lower housing 12B. The drug pump may further include an activation mechanism 14, a status indicator (not shown), and a window 18. Window 18 may be any translucent or transmissive surface through which the operation of the drug pump may be viewed. As shown in FIG. 1B, drug pump 10 further includes assembly platform 20, drive mechanism 100 having drug container 50, insertion mechanism 200, fluid pathway connection assembly 300, and power and control system 400. A sterile fluid conduit 30 (as in FIG. 30) may fluidly connect the fluid pathway connection assembly 300 with the insertion mechanism 200. One or more of the components of such drug pumps may be modular in that they may be, for example, pre-assembled as separate components and configured into position onto the assembly platform 20 of the drug pump 10 during manufacturing.

The pump housing 12 contains all of the device components and provides a means of removably attaching the device 10 to a target, such as tissue of a user. The pump housing 12 also provides protection to the interior components of the device 10 against environmental influences. The pump housing 12 is ergonomically and aesthetically designed in size, shape, and related features to facilitate easy packaging, storage, handling, and use by users who may be untrained and/or physically impaired. Furthermore, the external surface of the pump housing 12 may be utilized to provide product labeling, safety instructions, and the like. Additionally, as described above, housing 12 may include certain components, such as a status indicator (not shown) and window 18, which may provide operation feedback to the user.

In at least one embodiment, the drug pump 10 provides an activation mechanism 14 that is displaced by the user to trigger the start command to the power and control system 400. In a preferred embodiment, the activation mechanism is a start button 14 that is located through the pump housing 12, such as through an aperture in the upper housing 12A (as in FIG. 1A), or between upper housing 12A and lower housing 12B (not shown), and which contacts a control arm (not shown) of the power and control system 400. In at least one embodiment, the start button 14 may be a push button, and in other embodiments, may be an on/off switch, a toggle, or any similar activation feature known in the art. The pump housing 12 may also include a status indicator (not shown) and a window 18. In other embodiments, one or more of the activation mechanism 14, the status indicator, the window 18, and combinations thereof may be provided on the upper housing 12A or the lower housing 12B such as, for example, on a side visible to the user when the drug pump 10 is placed on the target. Housing 12 is described in further detail hereinafter with reference to other components and embodiments of the present invention.

Drug pump 10 is configured such that, upon activation by a user by depression of the activation mechanism, the drug pump is initiated to: insert a fluid pathway into the target; enable, connect, or open necessary connections between a drug container, a fluid pathway, and a sterile fluid conduit; and force drug fluid stored in the drug container through the fluid pathway and sterile fluid conduit for delivery into a target. Each of these operations may begin simultaneously upon depression of the activation mechanism or, alternatively, one or more operations may be delayed. The fluid pathway connection may be initiated directly by the user, or may be activated by another mechanism of the device (as described herein) after some initial user step.

One or more optional safety mechanisms may be utilized, for example, to prevent premature activation of the drug pump. For example, an optional on-body sensor 24 may be provided in one embodiment as a safety feature to ensure that the power and control system 400, or the activation mechanism 14, cannot be engaged unless the drug pump 10 is in contact with the target. In one such embodiment, the on-body sensor is located on the bottom of lower housing 12B where it may come in contact with the target. Upon displacement of the on-body sensor, depression of the activation mechanism is permitted. Accordingly, in at least one embodiment the on-body sensor 24 is a mechanical safety mechanism, such as for example a mechanical lock out, that prevents triggering of the drug pump 10 by the activation mechanism 14. In another embodiment, the on-body sensor may be an electro-mechanical sensor such as a mechanical lock out that sends a signal to the power and control system 400 to permit activation. In still other embodiments, the on-body sensor can be electrically based such as, for example, a capacitive- or impedance-based sensor which must detect tissue before permitting activation of the power and control system 400.

In at least one embodiment, housing 12 is configured to at least partially prevent harmful matter from entering the drug pump. For example, the housing may be configured to restrict the passage of fluids into the drug pump. This may allow the device to be worn in the shower, while swimming, or during other activities. Use of an electrically based skin sensor may eliminate potential points of entry into the drug pump. These concepts are not mutually exclusive and one or more combinations may be utilized within the breadth of the present invention to prevent, for example, premature activation of the drug pump. In a preferred embodiment, the drug pump 10 utilizes one or more mechanical on-body sensors. Additional integrated safety mechanisms are described herein with reference to other components of the novel drug pumps.

Power and Control System:

The power and control system 400 includes a power source, which provides the energy for various electrical components within the drug pump, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system 400 controls several device interactions with the user and interfaces with the drive mechanism 100. In one embodiment, the power and control system 400 interfaces with the control arm to identify when the on-body sensor 24 and/or the activation mechanism 14 have been activated. The power and control system 400 may also interface with the status indicator 16 of the pump housing 12, which may be a transmissive or translucent material which permits light transfer, to provide visual feedback to the user. The power and control system 400 interfaces with the drive mechanism 100 through one or more interconnects to relay status indication, such as activation, drug delivery, and end-of-dose, to the user. Such status indication may be presented to the user via auditory tones, such as through the audible alarms, and/or via visual indicators, such as through the LEDs. In a preferred embodiment, the control interfaces between the power and control system and the other components of the drug pump are not engaged or connected until activation by the user. This is a desirable safety feature that prevents accidental operation of the drug pump and may additionally maintain the energy contained in the power source during storage, transportation, and the like.

The power and control system 400 may be configured to provide a number of different status indicators to the user. For example, the power and control system 400 may be configured such that after the on-body sensor and/or trigger mechanism have been pressed, the power and control system 400 provides a ready-to-start status signal via the status indicator 16 if device start-up checks provide no errors. After providing the ready-to-start status signal and, in an embodiment with the optional on-body sensor, if the on-body sensor remains in contact with the target, the power and control system 400 will power the drive mechanism 100 to begin delivery of the drug treatment through the fluid pathway connection assembly 300 and sterile fluid conduit. In a preferred embodiment of the present invention, the insertion mechanism 200 and the fluid pathway connection assembly 300 may be caused to activate directly or indirectly by user operation of the activation mechanism 14. During the drug delivery process, the power and control system 400 is configured to provide a dispensing status signal via the status indicator 16. After the drug has been administered into the target and after the end of any additional dwell time, to ensure that substantially the entire dose has been delivered to the target, the power and control system 400 may provide an okay-to-remove status signal via the status indicator 16. This may be independently verified by the user by viewing the drive mechanism and drug dose delivery through the window 18 of the pump housing 12. Additionally, the power and control system 400 may be configured to provide one or more alert signals via the status indicator 16, such as for example alerts indicative of fault or operation failure situations.

Other power and control system configurations may be utilized with the novel drug pumps of the present invention. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism 14 of the drug pump 10 prior to drug pump activation. Additionally, the system may include a feature which permits the user to respond to the end-of-dose signals and to deactivate or power-down the drug pump. Such a feature may similarly require a delayed depression of the activation mechanism, to prevent accidental deactivation of the device. Such features provide desirable safety integration and ease-of-use parameters to the drug pumps. An additional safety feature may be integrated into the activation mechanism to prevent partial depression and, therefore, partial activation of the drug pumps. For example, the activation mechanism and/or power and control system may be configured such that the device is either completely off or completely on, to prevent partial activation. Such features are described in further detail hereinafter with regard to other aspects of the novel drug pumps.

Insertion Mechanism:

A number of insertion mechanisms may be utilized within the drug pumps of the present invention. In at least one embodiment, the insertion mechanism 200 includes an insertion mechanism housing having one or more lockout windows, and a base for connection to the assembly platform and/or pump housing (as shown in FIG. 1B and FIG. 1C). The connection of the base to the assembly platform 20 may be, for example, such that the bottom of the base is permitted to pass-through a hole in the assembly platform to permit direct contact of the base to the target, as shown in FIG. 1C. In such configurations, the bottom of the base may include a sealing membrane that is removable prior to use of the drug pump 10. The insertion mechanism may further include one or more insertion biasing members, a needle, a retraction biasing member, a cannula, and a manifold. The manifold may connect to sterile fluid conduit to permit fluid flow through the manifold, cannula, and into the target during drug delivery.

As used herein, "needle" is intended to refer to a variety of needles including but not limited to conventional hollow needles, such as a rigid hollow steel needles, and solid core needles more commonly referred to as a "trocars." In some embodiments, the needle is a 27 gauge solid core trocar and in other embodiments, the needle may be any size needle suitable to insert the cannula for the type of drug and drug administration (e.g., subcutaneous, intramuscular, intradermal, etc.) intended. In one embodiment, the insertion mechanism may generally be as described in International Patent Application No. PCT/US2012/53174 published as WO 2013/033421 A2, International Patent Application No. PCT/US2012/053241 published as WO 2013/033467 A2 or International Patent Application No. PCT/US2015/052815, which are included by reference herein in their entirety for all purposes.

Drive Mechanism:

A number of drive mechanisms may be utilized to force fluid from a drug container 50 for delivery into the target. In one such embodiment, the drive mechanism 100 includes a drive housing, a status switch interconnect, and a drug container 50 having a crimp cap 324, a pierceable seal 326, a barrel 58, and a plunger seal 60 within the barrel. The drug container may contain a drug fluid, within the barrel between the pierceable seal and the plunger seal, for delivery through the insertion mechanism and drug pump into the target. The seals described herein may be comprised of a number of materials but are, in a preferred embodiment, comprised of one or more elastomers or rubbers. The drive mechanism may further include a connection mount to guide the insertion of the piercing member of the fluid pathway connection assembly into the barrel 58 of the drug container. The drive mechanism 100 may further contain one or more drive biasing members, one or more release mechanisms, and one or more guides. The components of the drive mechanism function to force a fluid from the drug container out through the pierceable seal, or preferably through the piercing member of the fluid pathway connection assembly, for delivery through the fluid pathway connection assembly, sterile fluid conduit, and insertion mechanism into the target.

In one particular embodiment, the drive mechanism 100 employs one or more compression springs as the biasing member(s). Upon activation of the drug pump by the user, the power and control system 400 may be actuated to directly or indirectly release the compression spring(s) from an energized state. Upon release, the compression spring(s) may bear against and act upon the plunger seal to force the fluid drug out of the drug container. The fluid pathway connection assembly 300 may be connected through the pierceable seal prior to, concurrently with, or after activation of the drive mechanism to permit fluid flow from the drug container, through the fluid pathway connection assembly, sterile fluid conduit, and insertion mechanism, and into the target for drug delivery. In at least one embodiment, the fluid flows through only a manifold or a needle, and a cannula, of the insertion mechanism, thereby maintaining the sterility of the fluid pathway before and during drug delivery. Such components and their functions are described in further detail hereinafter.

The components of the drive mechanism 100, upon activation, may be used to drive axial translation in the distal direction of the plunger seal of the drug container. Optionally, the drive mechanism 100 may include one or more compliance features which enable additional axial translation of the plunger seal to, for example, ensure that substantially the entire drug dose has been delivered to the target and make sure that the feedback contact mechanisms have connected. Additionally or alternatively, the plunger seal, itself, may have some compressibility permitting a compliance push of drug fluid from the drug container. The drive mechanism 100 may similarly include one or more status indication mechanisms, such as interconnects and contacts, to measure and communicate the status of the drive mechanism before, during, and after operation of the drive mechanism and the device to the user. Furthermore, the drive mechanism 100 may include one or more safety mechanisms, such as premature activation prevention mechanisms, to enhance the safety and usability of the mechanism and the device. Further details related to the drive mechanism 100 are provided herein with reference to other components of the drug pump. In one embodiment, the insertion mechanism may generally be as described in International Patent Application No. PCT/US2012/05174 published as WO 2013/033421 A2 or International Patent Application No. PCT/US2013/057259 published as WO 2014-036239 A2, which are included by reference herein in their entirety for all purposes.

Fluid Pathway Connection Assembly:

Embodiments of the present fluid pathway connection assemblies allow connections to be made between two or more components or subassemblies in a septic environment while maintaining the aseptic condition of the fluid flow path. As will be seen, the fluid pathway connection assemblies may be arranged in any orientation. For example, as illustrated in FIGS. 2A-10, the piercing member may be axially aligned with the drug container. In other embodiments, as shown in FIGS. 22-29, the fluid pathway connection assembly may be arranged such that the piercing member of the fluid pathway connection assembly is oriented at an angle with respect to the drug container. In an alternative embodiment, the piercing member may be arranged in an arcuate manner. An exemplary embodiment of such an arrangement is shown in FIGS. 11A-21. The orientation of the fluid pathway connection assembly may be chosen based on the desired overall size and shape of drug pump 10 and the available space within the drug pump.

Figure 2A:
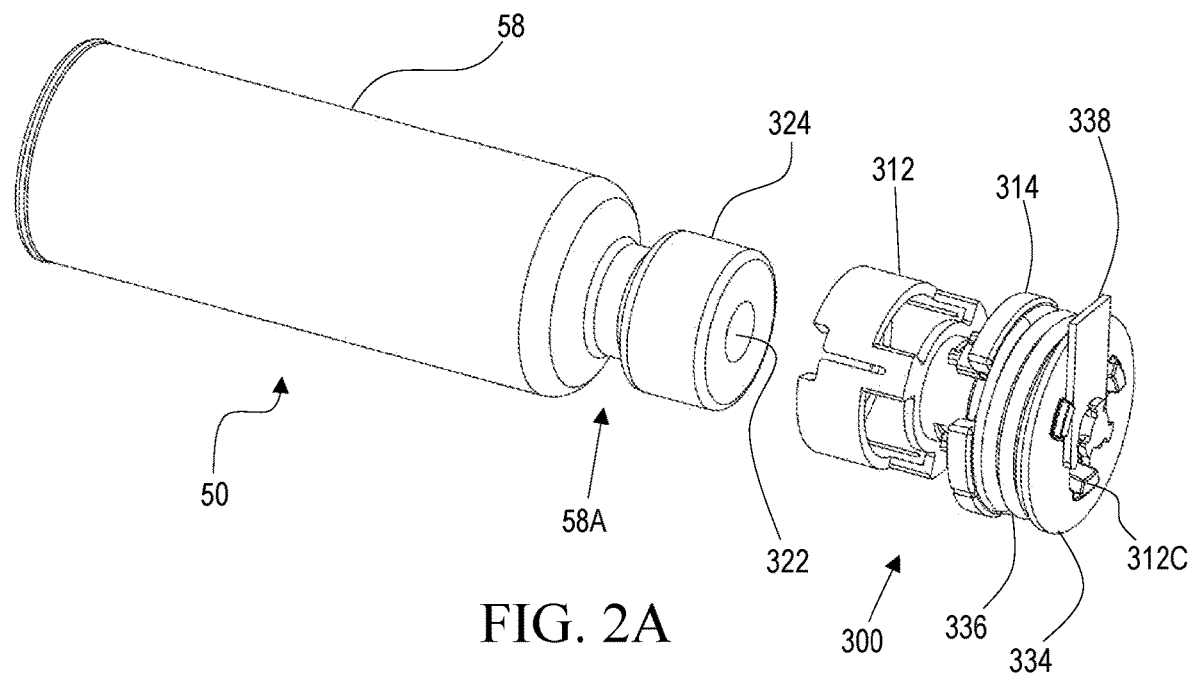
FIG. 2A is an isometric view of an embodiment of a fluid pathway connection assembly and drug container in an unmounted configuration.

FIGS. 2A-10 show one embodiment of such a fluid pathway connection assembly. As seen in FIGS. 2A-2B, the fluid pathway connection assembly 300 may be connected to the drug container 50. FIG. 2A shows these components prior to connection and FIG. 2B shows the components after connection. As will be described herein, fluid pathway connection assembly 300 may be mounted to drug container 50 without compromising the aseptic condition of the fluid flow path. Fluid pathway connection assembly 300 includes introducer member 320, piercing member 316, introducer member retainer 330, piercing member retainer 314, connection hub 312, plate 334, biasing member 336, sterile boot 340, and first film 318. FIGS. 3A-3B show exploded views of the fluid pathway connection assembly 300.

According to one aspect of the invention (see FIGS. 4A and 4B), the connection hub 312 includes a cavity 312A. Sterile boot 340 may further define the cavity 312A as aseptic. In one embodiment, sterile boot 340 is fixedly connected at a first end to connection hub 312 and at a second end to introducer member retainer 330. Sterile boot 340 may be constructed from a flexible material, such as an elastomer, thereby allowing the sterile boot to deform to maintain engagement with both connection hub 312 and introducer member retainer 330 during operation. A first film 318 is disposed covering an aperture 312B of connection hub 312 to prevent microbes and other contaminants from entering cavity 312A through aperture 312B. In this way, the area contained or bounded by the sterile boot 340, the connection hub 312, and the first film 318 defines cavity 312A and maintains the aseptic condition of the cavity 312A.

Figure 2B:
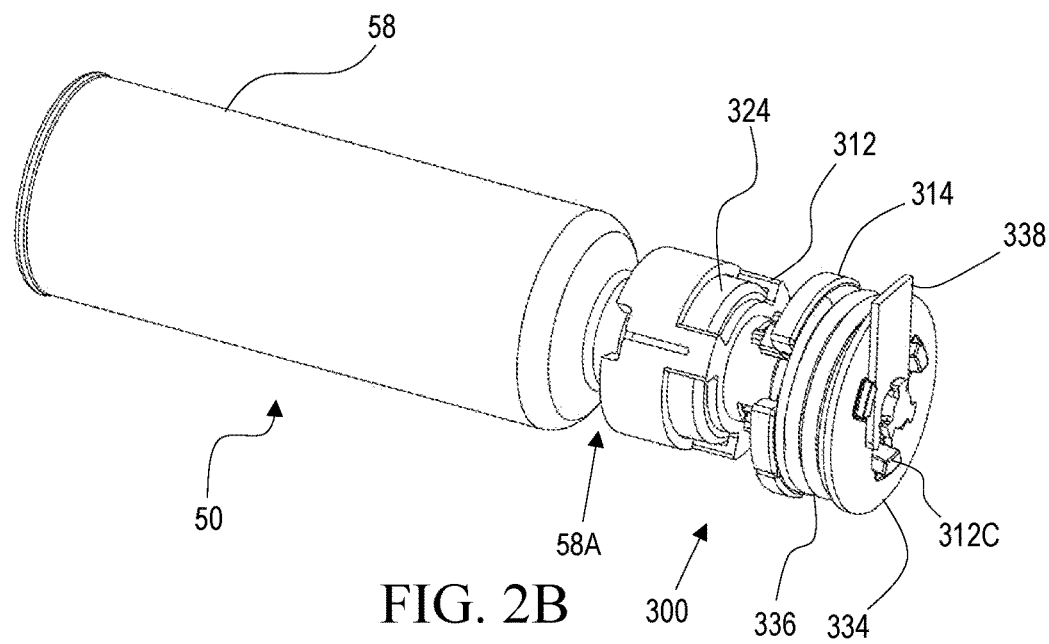
FIG. 2B is an isometric view of the embodiment shown in FIG. 2A in a mounted, but unactuated, configuration.
Figure 3A:
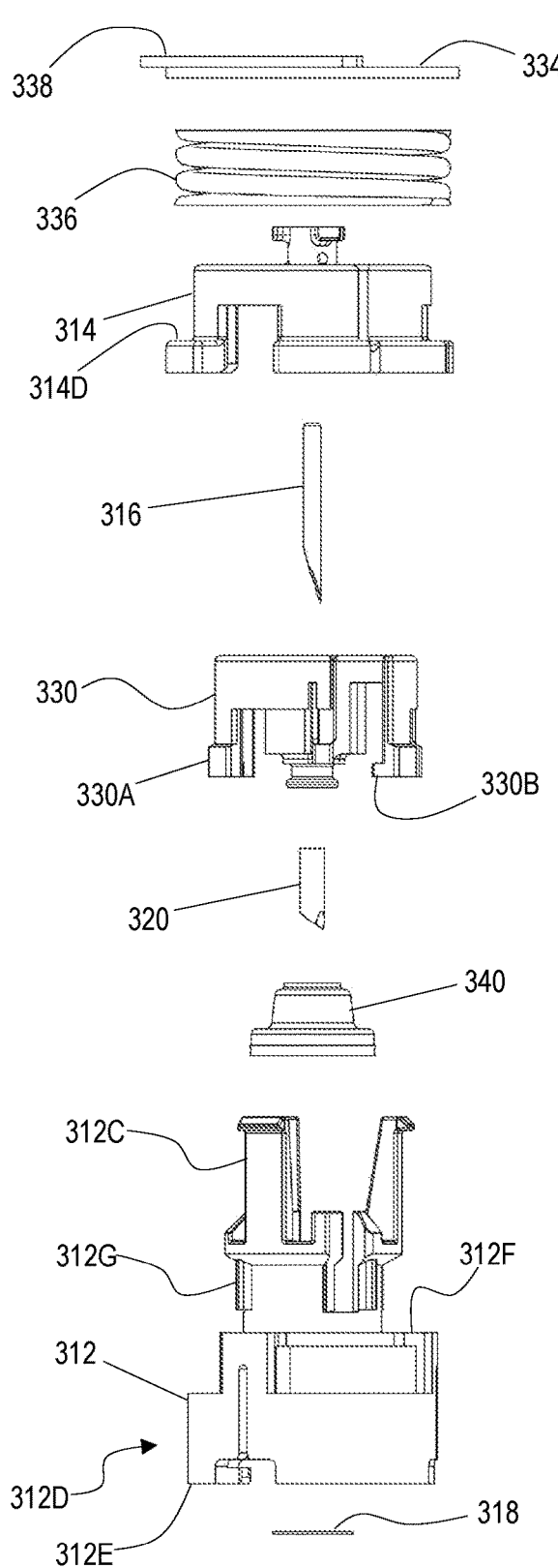
FIG. 3A shows an exploded view of a fluid pathway connection assembly according to at least one embodiment of the present invention.
Figure 3B:
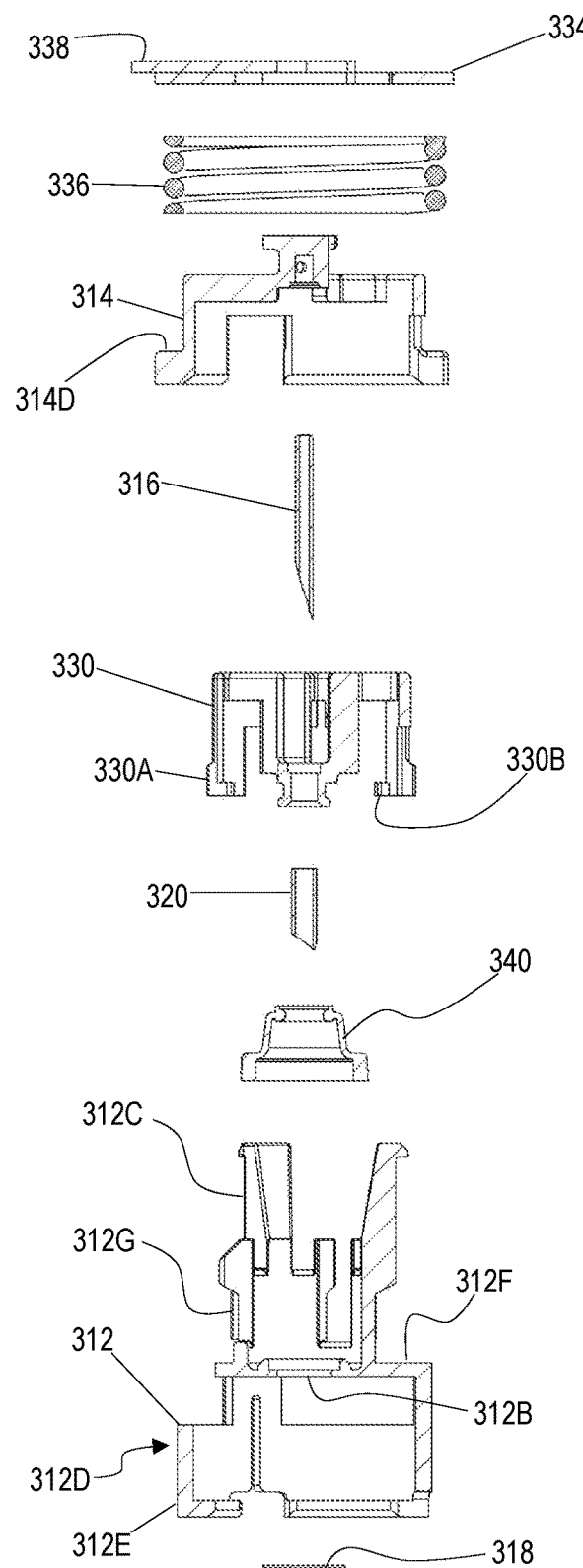
FIG. 3B shows a cross-sectional view of the exploded fluid pathway connection assembly of FIG. 3A.
Figure 4A:
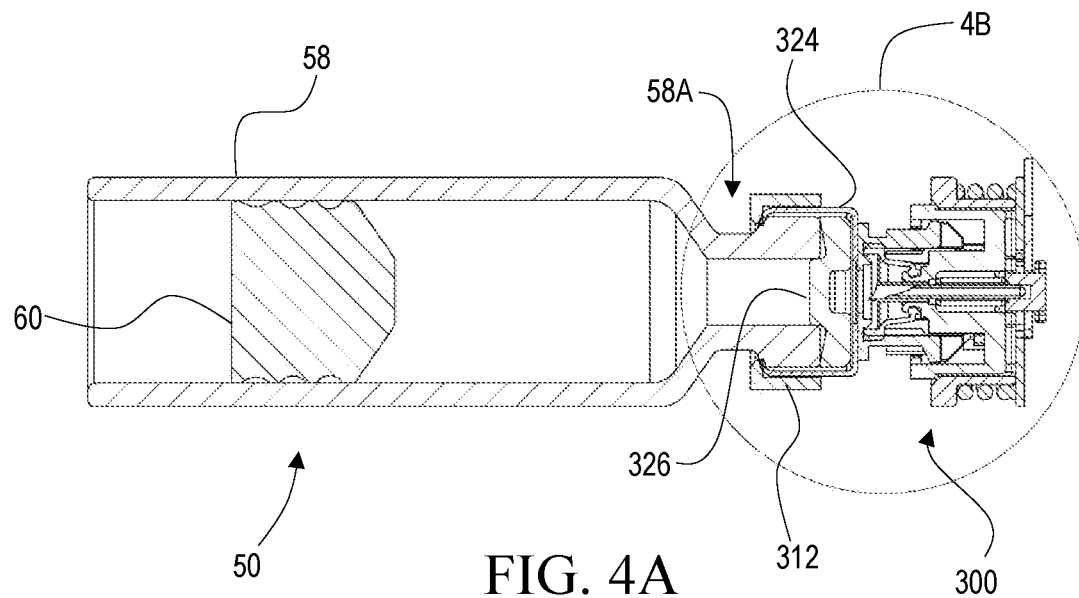
FIG. 4A is a cross-sectional side view of an embodiment of a fluid pathway connection assembly and a drug container in a mounted, but unactuated, configuration.
Figure 4B:
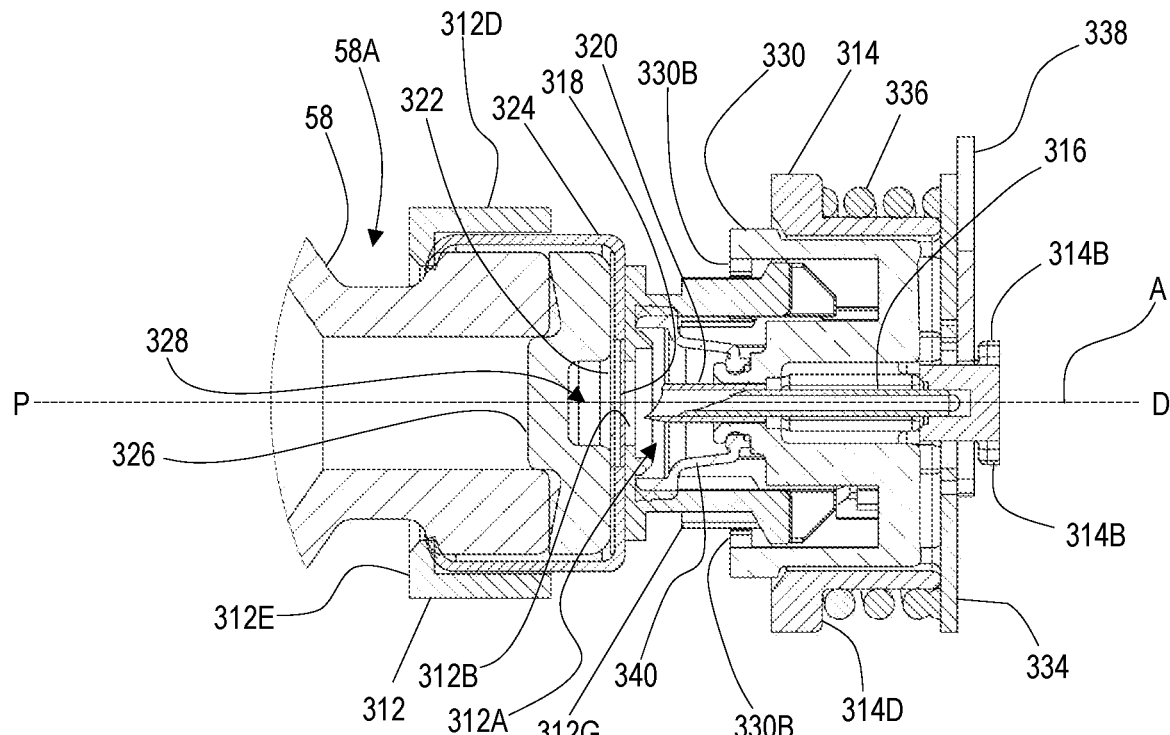
FIG. 4B is an enlarged fragmentary cross-sectional side view of the embodiment shown in FIG. 4A.

In an unmounted configuration, such as illustrated in FIG. 2B, and in an initial, unactuated configuration, as shown in FIGS. 4A-4B, at least a portion of introducer member 320 is disposed within aseptic cavity 312A. At least a piercing tip of the piercing member 316 is partially retained within lumen 320A of introducer member 320, the piercing member 316 being disposed to telescope within the introducer member 320. The piercing member 316 is also at least partially disposed in piercing member retainer 314. In this way, introducer member 320 and piercing member 316 are likewise maintained in an aseptic condition within cavity 312A.

Piercing member 316 is engaged with piercing member retainer 314 such that translation of piercing member retainer 314 is transferred to piercing member 316 such that they maintain a substantially fixed spatial relationship throughout operation. Piercing member 316 may be engaged with piercing member retainer 314 using any method known to one skilled in the art, such as bonding, press-fit, staking, etc. The piercing member 316 may be, for example, a hollow needle.

Introducer member 320 is at least partially retained by introducer member retainer 330 and is engaged with the introducer member retainer 330 such that translation of introducer member retainer 330 is transferred to introducer member 320 such that they maintain a substantially fixed spatial relationship throughout operation. Introducer member 320 may be engaged with introducer member retainer 330 using any method known to one skilled in the art, such as bonding, press-fit, staking, or any other appropriate method.

Piercing member retainer 314 and introducer member retainer 330 are engaged with connection hub 312 and may be configured for translation with respect to the connection hub in a direction parallel to the long axis of piercing member 316 (axis "A" shown in FIG. 4B). Connection hub 312, piercing member retainer 314, and introducer member retainer 330 may include one or more features to maintain orientation and position with respect to one another as will be described in more detail below.

The fluid pathway connection assembly 300 may further be provided with an insertion driver disposed to advance one or both of the piercing member 316 and the introducer member 320 toward the drug container 50. In this embodiment, at least one biasing member 336 is provided to advance one or both of the piercing member 316 and the introducer member 320 toward the drug container 50. Biasing member 336 is initially in a compressed or energized condition and is restrained from decompressing or de-energizing. A first end of biasing member 336 is in contact with plate 334, which is axially stationary, and a second end of biasing member 336 is in contact with piercing member retainer 314. In one embodiment, biasing member 336 is in contact with shoulder 314D of piercing member retainer 314. Motion of plate 334 is restrained by engagement with snaps 312C of connection hub 312 (see FIG. 7) which are inserted through passages 334A of plate 334 (see FIG. 8) during assembly. In an initial configuration, shaft 314A of piercing member retainer 314 (see FIG. 9) passes through central bore 334B of plate 334 and is engaged by interlock 338 (see FIGS. 2A, 2B, 4A, 4B). Interlock 338 is located on the distal side of plate 334 and engages one or more lobes 314B on shaft 314A to prevent translation of piercing member retainer 314 with respect to plate 334. In this way, decompression or de-energizing of biasing member 336 is restrained. As will be described further herein, transformation of interlock 338, to a configuration in which it does not restrain translation of piercing member retainer 314, allows decompression of biasing member 336 and connection of the fluid pathway to drug container 50.

The drug container 50 may include a crimp cap 324 that maintains a connection between a pierceable seal 326 and a barrel 58. The pierceable seal maintains the fluid drug within the barrel and prevents microbes and other substances from entering the drug chamber. A recess 328 (best seen in FIG. 4B) is formed by the geometry of the pierceable seal 326. A second film 322 is affixed to the drug container such that it encloses recess 328, thereby maintaining recess 328 in an aseptic condition.

The first and second films may be constructed of any material capable of providing the barrier properties required to maintain the aseptic condition of the associated surfaces. In a preferred embodiment, the films are constructed from a foil material. Alternatively, the films may be any type of sterilizable membrane, film, or foil. Additionally, the film may be removable and/or pierceable as well as breathable and/or permeable.

A surface treatment may be applied to the exterior surfaces of both first film 318 and second film 322 prior to joining the fluid pathway connection assembly and the drug container. The surface treatment may contain antimicrobial, antibacterial, or antiviral compounds to limit or reduce the number of such substances on the surface of the seals.

Connection hub 312 may include a barrel-engaging aspect 312D. Barrel-engaging aspect 312D may include one or more flex arms 312E configured to engage crimp cap 324 and/or neck 58A of barrel 58. During connection, flex arms 312E may engage crimp cap 324 or another portion of the drug container, thereby limiting axial translation of the fluid pathway connection assembly with respect to the drug container. In this position, first film 318 and second film 322 are in contact with, or in close proximity to, one another. In one embodiment, first film 318 and second film 322 include an adhesive such that the films are bonded to one another during assembly.

FIGS. 4A-4B show a cross-sectional side view of the connection hub 312 and drug container 50 in a mounted, unactuated configuration, that is, after they have been joined. In this configuration, introducer member 320 is at least partially disposed within cavity 312A and engagement of interlock 338 with piercing member retainer 314 retains biasing member 336 in a compressed or energized state. First film 318 and second film 322 are intact, thereby maintaining the aseptic condition of cavity 312A and pierceable seal 326, respectively.

Figure 5A:
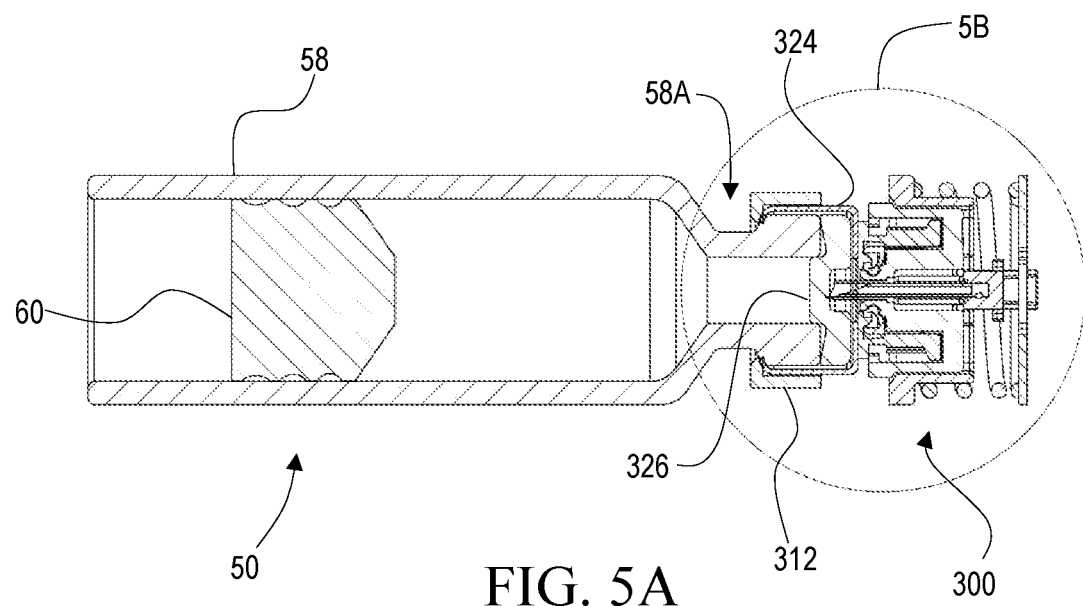
FIG. 5A is a cross-sectional side view of the embodiment of the fluid pathway connection assembly and drug container of FIG. 4A in an actuated configuration.
Figure 5B:
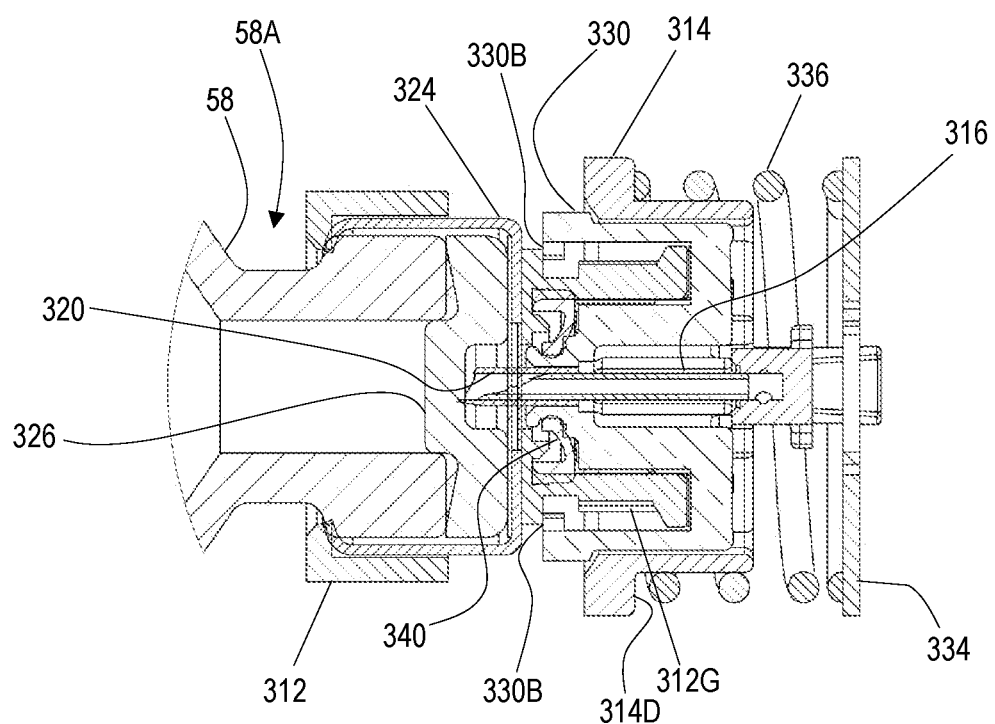
FIG. 5B is an enlarged fragmentary cross-sectional side view of the embodiment shown in FIG. 5A.

An actuated configuration is illustrated in FIGS. 5A-5B. In one embodiment, activation may displace or transform interlock 338 such that it no longer restricts translation of piercing member retainer 314. Upon activation, the piercing member retainer 314 and introducer member retainer 330 may be translated axially with respect to the connection hub and drug container 50. The translation may be caused by decompression or de-energizing of biasing member 336. In one embodiment, biasing member 336 is a compression spring. Because piercing member retainer 314 is in contact with introducer member retainer 330, as piercing member retainer 314 translates, introducer member retainer 330 translates together with piercing member retainer 314. For example, proximal face 314C of piercing member retainer 314 (see FIG. 9) may contact projections 330A of introducer member retainer 330 (see FIG. 10). Proximal face 314C may include a chamfered or radiused portion which contacts projections 330A. The contacting faces of piercing member retainer 314 and introducer member retainer 330 may be configured such that piercing member retainer 314 applies a radially inwardly directed force to projections 330A and, thereby, extensions 330D, in addition to an axial force. However, initially, fingers 330C of extensions 330D are prevented from inward displacement by contact with ribs 312G of connection hub 312 (see FIGS. 3A, 3B, 5B). Hence, introducer member retainer 330 translates along with piercing member retainer 314. Translation of the piercing member retainer 314 causes piercing member 316 to translate and translation of the introducer member retainer 330 causes translation of the introducer member 320. This translation causes the introducer member 320 to pierce first film 318 and second film 322, as shown in FIGS. 5A-5B. It will be appreciated that, because the piercing member 316 is disposed within introducer member 320, it does not contact the first 318 and second 322 films; hence, any contaminants present on the surface of the films do not come in contact with the piercing member 316.

After the introducer member 320 pierces first film 318 and second film 322, translation of introducer member retainer 330 is restricted such that its translation is terminated with the tip of the introducer member disposed in recess 328 (i.e., the introducer member does not pass through pierceable seal 326). Translation of introducer member retainer 330 may, for example, be restricted by contact of a portion of the proximal face 330B with flange 312F of connection hub 312. It is not necessary that the entire proximal face 330B of introducer member retainer 330 contact flange 312F. For example, fingers 330C may contact flange 312F. In this position, fingers 330C are no longer in contact with ribs 312G of connection hub 312. Because of this, extensions 330D are able to flex radially inward. As a result, continued decompression of biasing member 336 and translation of piercing member retainer 314 causes the extensions 330D to move inward and piercing member retainer 314 is able to pass over introducer member retainer 330.

Figure 6A:
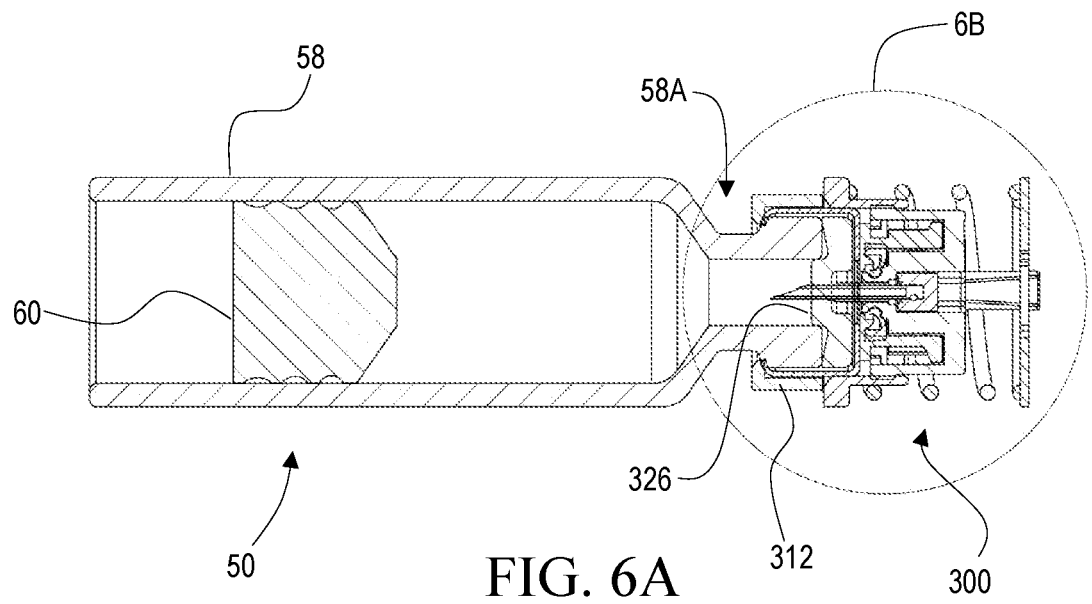
FIG. 6A is a cross-sectional side view of the embodiment of the fluid pathway connection assembly and drug container of FIGS. 4A and 5A in a delivery configuration.
Figure 6B:
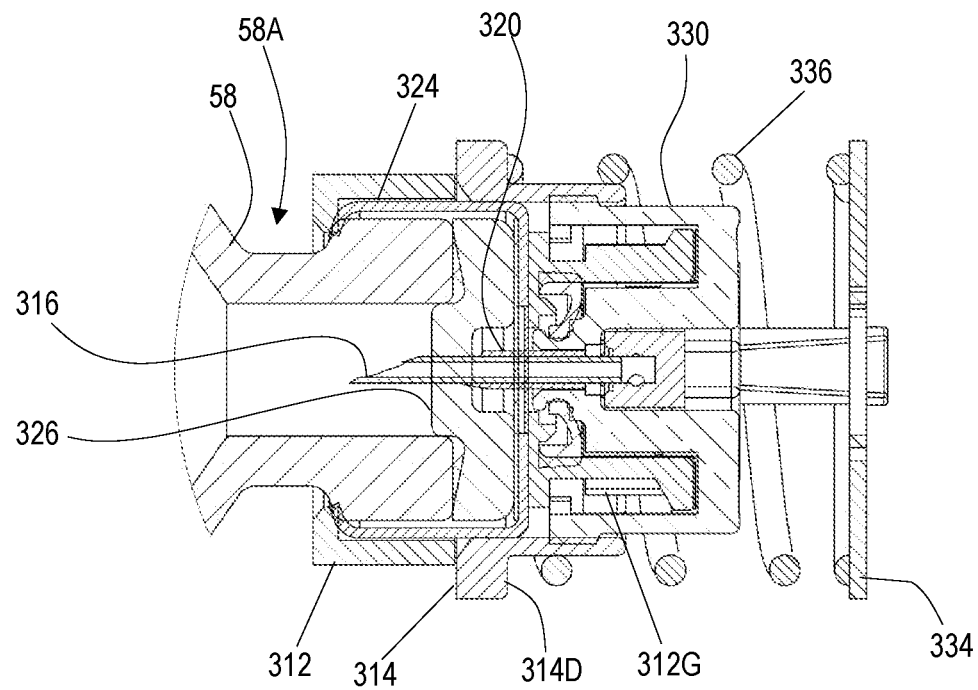
FIG. 6B is an enlarged fragmentary cross-sectional side view of the embodiment shown in FIG. 6A.
Figure 7:
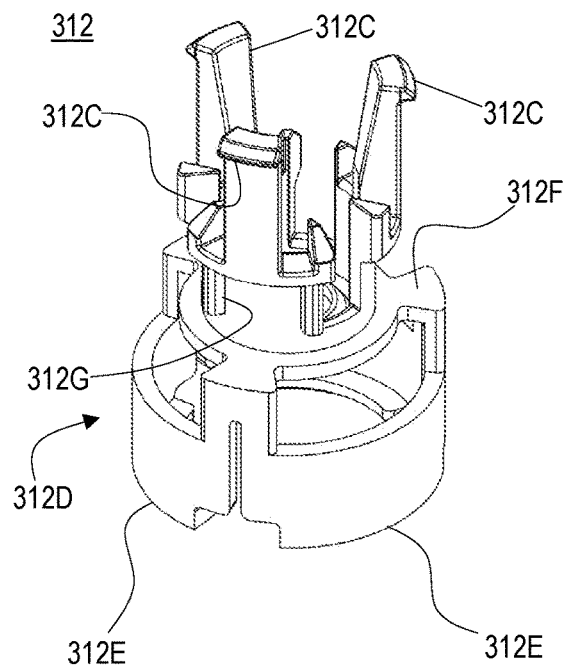
FIG. 7 shows an isometric view of a connection hub according to at least one embodiment of the present invention.
Figure 8:
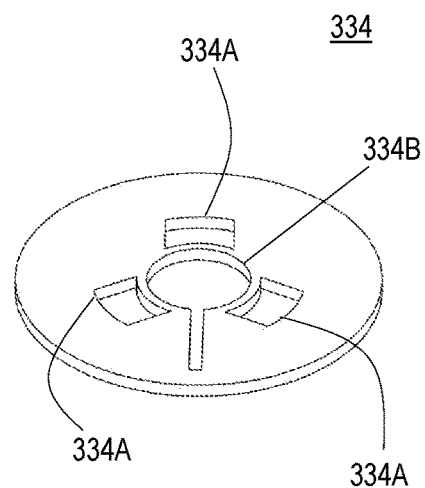
FIG. 8 shows an isometric view of a plate according to at least one embodiment of the present invention.
Figure 9:
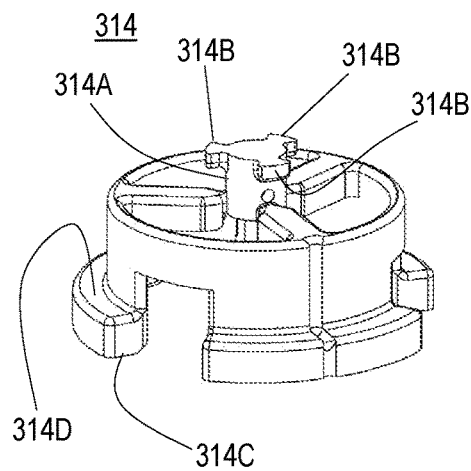
FIG. 9 shows an isometric view of an embodiment of a piercing member retainer according to at least one embodiment of the present invention.
Figure 10:
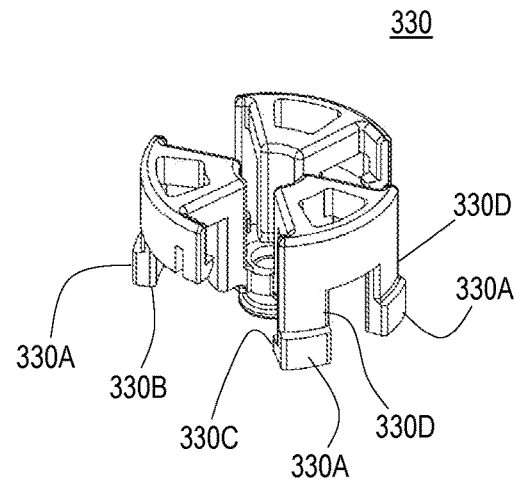
FIG. 10 shows an isometric view of an embodiment of an introducer member retainer according to at least one embodiment of the present invention.
Figure 11A:
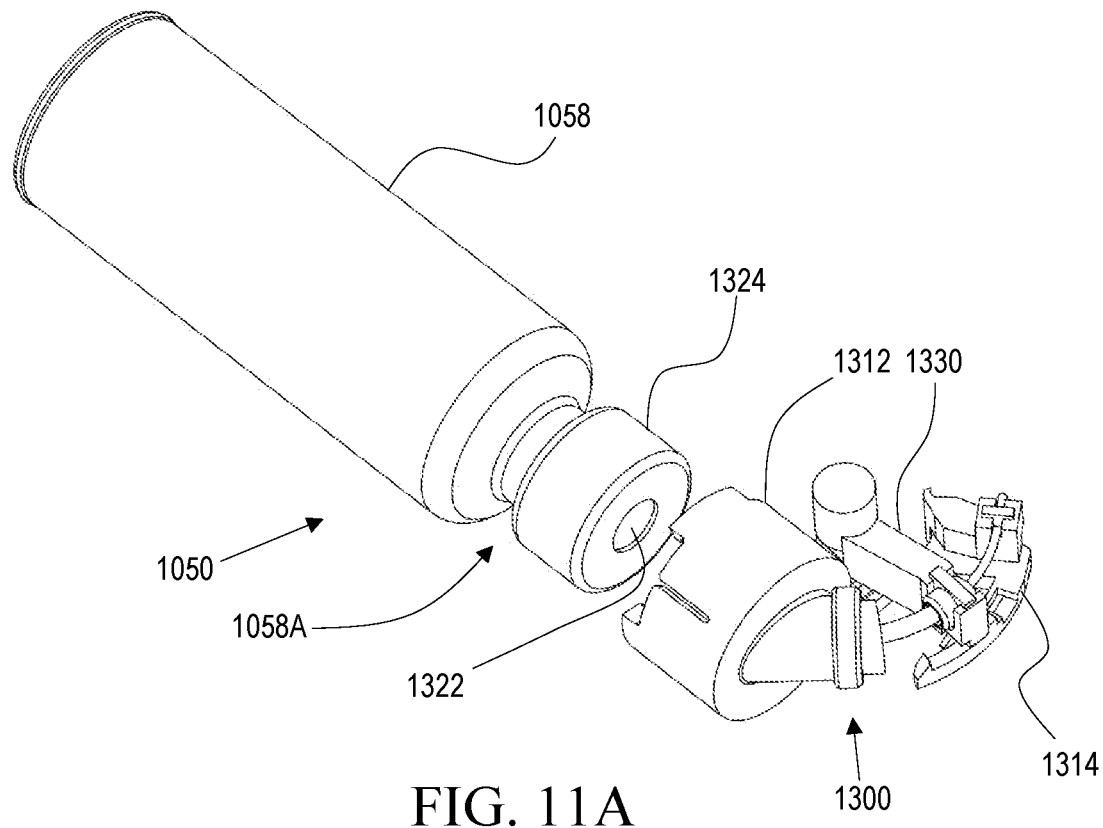
FIG. 11A is an isometric view of a second embodiment of a fluid pathway connection assembly and drug container in an unmounted configuration.
Figure 11B:
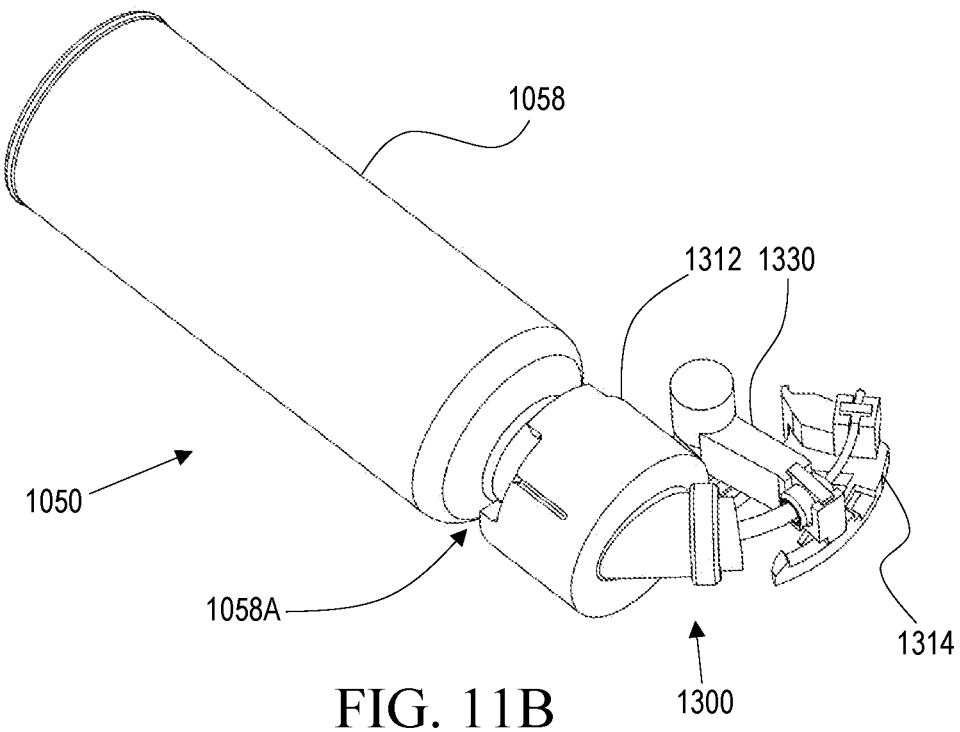
FIG. 11B is an isometric view of the embodiment shown in FIG. 11A in a mounted, but unactuated, configuration.

Turning now to FIGS. 6A-6B, there is illustrated a delivery configuration of the fluid pathway connection assembly 300. Continued decompression of biasing member 336 may cause the piercing member retainer 314 to be further displaced, leading to the piercing of pierceable seal 326 by piercing member 316. Hence, with further translation of introducer member retainer 330 prevented by contact with connection hub 312, continued decompression of biasing member 336 causes piercing member retainer 314 to translate in a proximal direction relative to introducer member retainer 330. After piercing of the pierceable seal, a fluid path is established from the drug container and through the piercing member 316. Those of skill in the art will appreciate that the piercing member 316 may also be in fluid communication with a conduit 30 (as in FIG. 30), the conduit being configured to carry the fluid contents to a delivery mechanism, such as an insertion mechanism, for delivery to a patient.

In an alternative embodiment, piercing of the first and second films occurs at the time of assembly. In such an embodiment, piercing of the pierceable seal at or near the time-of-use may be initiated by interaction with an activation mechanism.

In at least one embodiment, the first and second films are pierced by the introducer member at a first time, for example time of assembly, and the piercing member pierces the pierceable seal at a later time, for example upon activation. In such an embodiment, the end of the piercing member may remain disposed within recess 328 until time-of-use. The pierceable seal may be configured such that, in response to hydraulic and/or pneumatic pressure within the drug chamber, pierceable seal 326 deforms or is displaced and is caused to come into contact with the piercing member. This deformation of the pierceable seal 326 leads to the piercing of the seal by the piercing member 316. In such an embodiment, introducer member 320 may be retracted after piercing the first and second films.

Although the embodiment shown in FIGS. 2A-10 is configured such that piercing member 316 is substantially axially aligned with drug container 50, one skilled in the art would recognize that this orientation can be configured in any orientation. For example, the axis of piercing member 316 may be oriented orthogonal to the central axis of the drug container 50. Alternatively, the axes may be oriented at any angle between parallel and orthogonal. Selection of this angle or orientation may be chosen based on the space requirements of drug pump 10.

In another embodiment, shown in FIGS. 11A-21, the introducer member and piercing member are arranged in an arcuate manner. The arcuate configuration of the fluid pathway connection assembly may allow the footprint of the fluid pathway connection assembly to be reduced, allowing for a smaller overall size of drug pump 10. Fluid pathway connection assembly 1300 includes introducer member 1320, piercing member 1316, introducer member retainer 1330, piercing member retainer 1314, connection hub 1312, shaft 1342, and first film 1318. As described above, connection hub 1312 may be configured to engage drug container 1050, for example, by engaging crimp cap 1324 and/or neck 1058A of drug container 1050.

Introducer member 1320 may be either directly or indirectly coupled to introducer member retainer 1330. For example, in the embodiment shown, introducer member 1320 is fixedly connected to first sleeve 1344. In turn, first sleeve 1344 is engaged with second sleeve 1346. Finally, second sleeve 1346 is engaged with introducer member retainer 1330, for example by the keyed engagement shown. First sleeve 1344 and second sleeve 1346 may further retain septum 1348, through which piercing member 1316 may pass.

Similarly, piercing member 1316 may be directly or indirectly coupled to piercing member retainer 1314. In the embodiment shown, piercing member 1316 is engaged with keeper 1350. Keeper 1350 is engaged with piercing member retainer 1314 by, for example, the keyed arrangement shown.

Figure 12A:
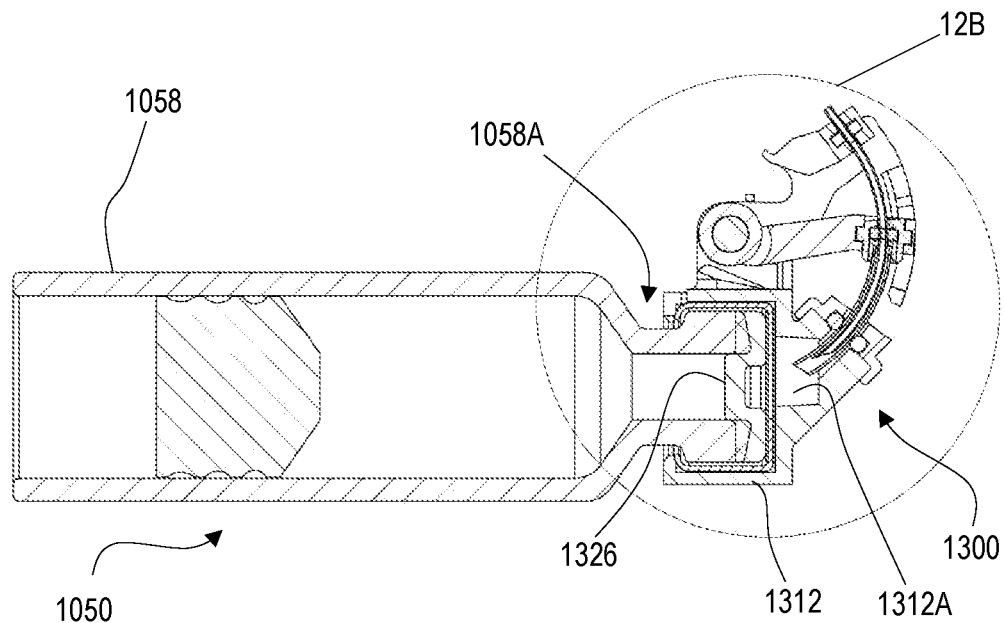
FIG. 12A is a cross-sectional side view of the embodiment of the fluid pathway connection assembly and drug container of FIGS. 11A-11B in a mounted, but unactuated, configuration.
Figure 12B:
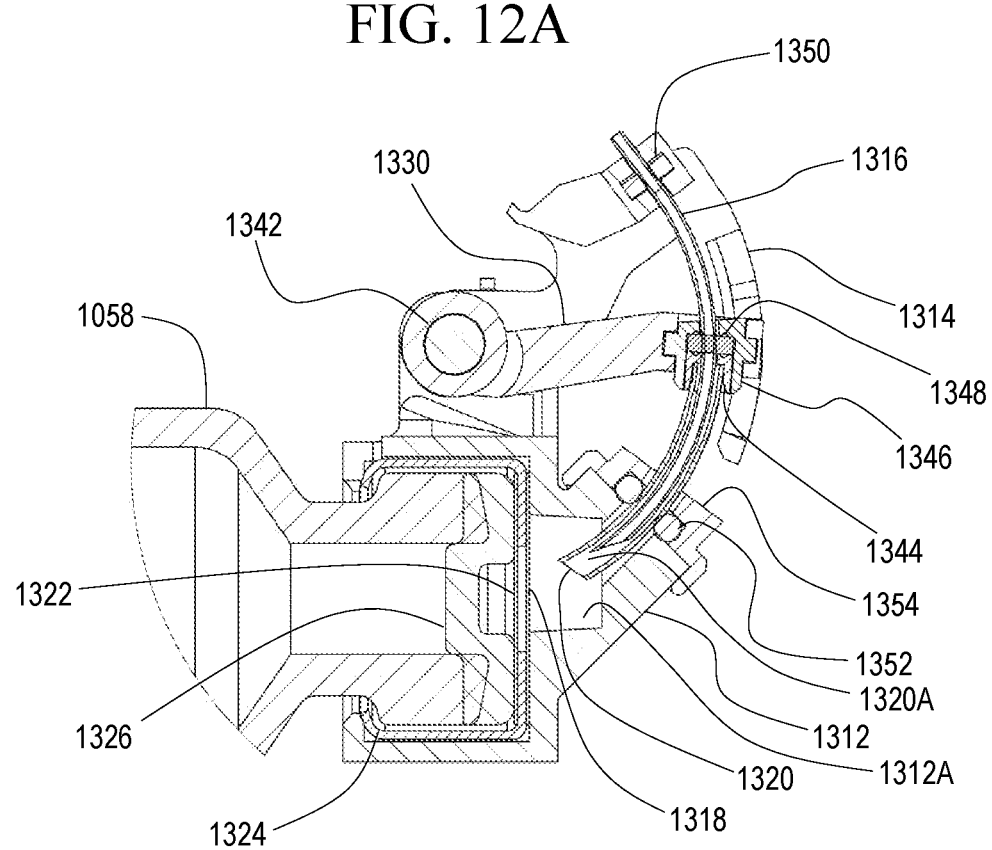
FIG. 12B is an enlarged fragmentary cross-sectional side view of the embodiment shown in FIG. 12A.
Figure 13A:
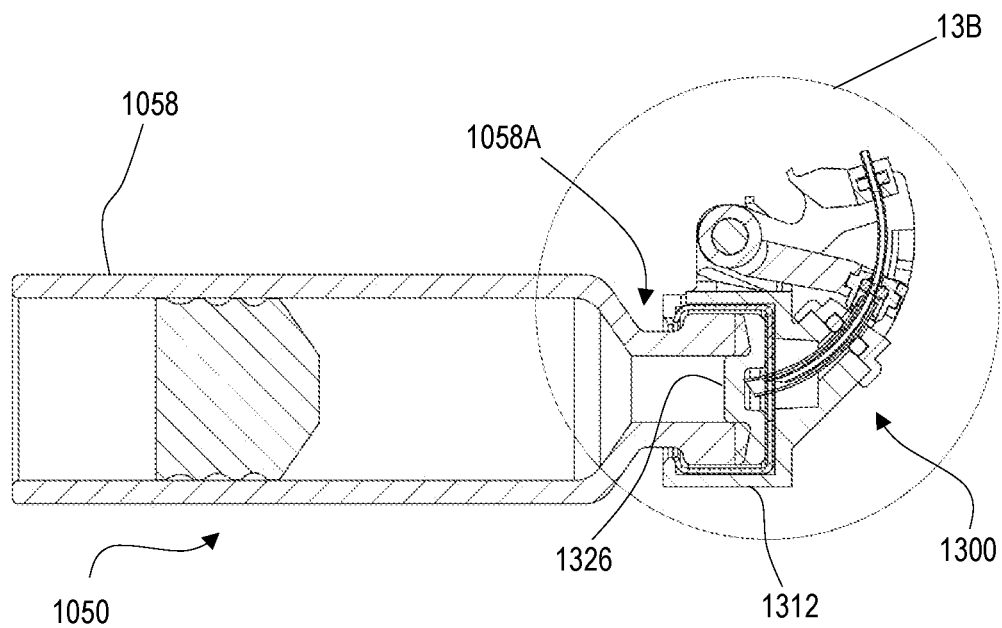
FIG. 13A is a cross-sectional side view of the embodiment of the fluid pathway connection assembly and drug container of FIG. 12A in an actuated configuration.
Figure 13B:
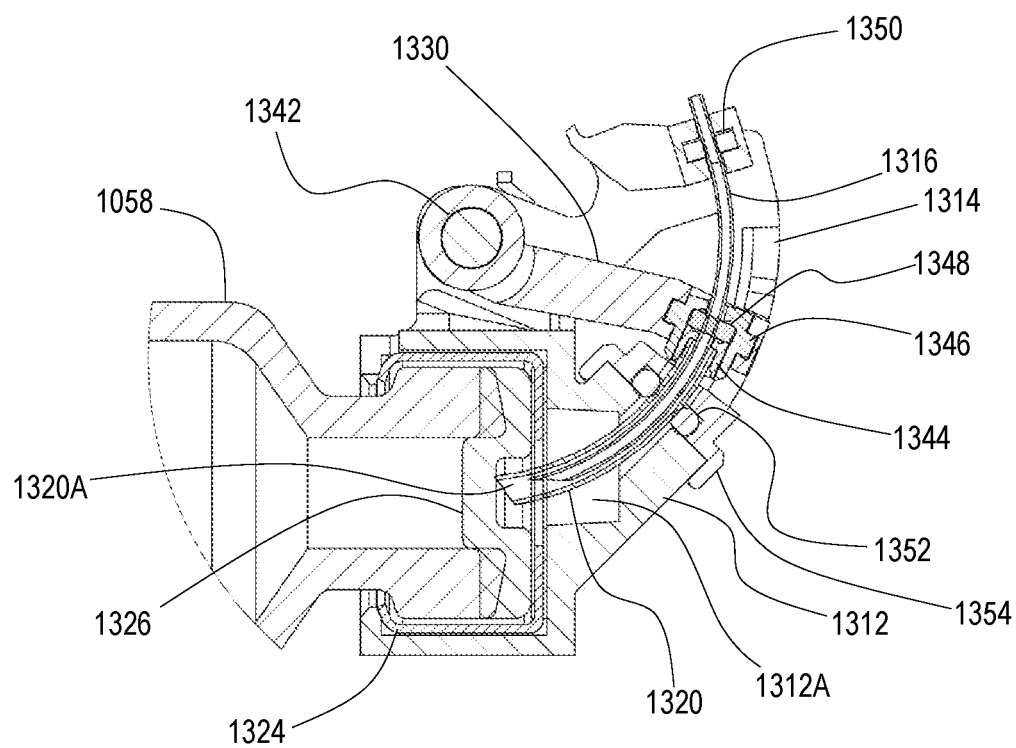
FIG. 13B is an enlarged fragmentary cross-sectional side view of the embodiment shown in FIG. 13A.

In an initial, unactuated configuration, shown in FIGS. 12A-12B, introducer member 1320 is initially at least partially disposed in cavity 1312A. Piercing member 1316 is at least partially disposed within the lumen 1320A of introducer member 1320. Cavity 1312A is maintained in an aseptic condition by first film 1318. The aseptic condition of cavity 1312A may be further maintained by cap 1354 and ring seal 1352. Ring seal 1352 is held in sealing engagement with connection hub 1312 and/or introducer member 1320 by cap 1354. Although ring seal 1352 is shown here with a circular cross-section, the ring seal may take on any shape known to one skilled in the art. Alternatively, for example, the aseptic condition may be maintained by a septum.

Upon activation, introducer member retainer 1330 and piercing member retainer 1314 are caused to rotate about shaft 1342. It will be appreciated that shaft 1342 may be integrally formed with connection hub 1312, as shown in FIG. 19, may be a feature of housing 12, or may be a pin or other component engaged with connection hub 1312 or housing 12. While the latter two of these embodiments are not specifically illustrated, they will be readily understood by those of skill in the art. An insertion driver may be provided to advance one or both of the piercing member 1316 and the introducer member 1320 toward the drug container 1050. For example, the rotation about the axis of the shaft may be caused by de-energizing of a biasing member, such as a torsion spring. Alternatively, the rotation may be caused by a driving member of drug pump 10. For example, needle insertion mechanism 200 may include a driving member that, upon activation, contacts an aspect of piercing member retainer 1314 and causes rotation of piercing member retainer 1314 and introducer member retainer 1330. In another embodiment, the biasing member of the needle insertion mechanism bears against the piercing member retainer 1314 and causes rotation thereof.

Figure 15A:
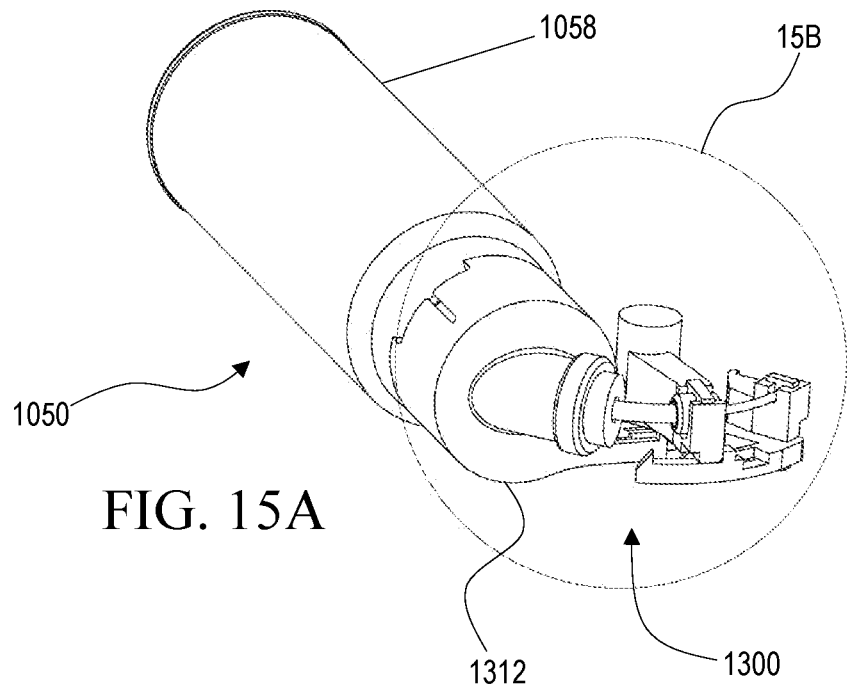
FIG. 15A is a further isometric view of the fluid pathway connection assembly and container of FIGS. 11A-11B in a mounted, but unactuated, configuration.
Figure 15B:
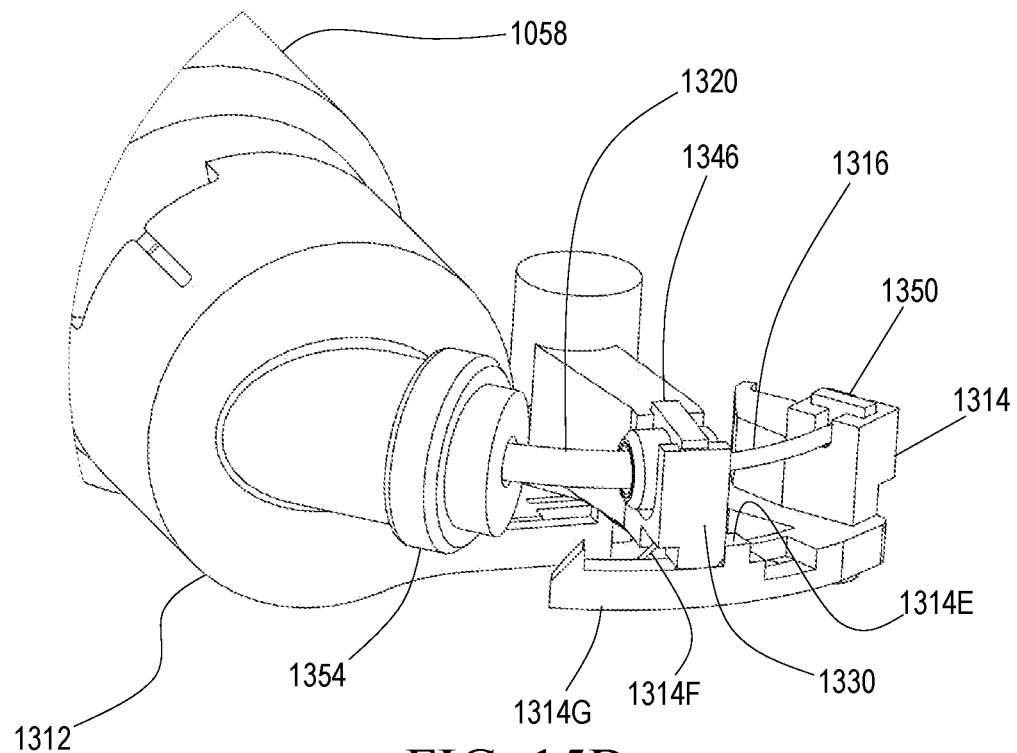
FIG. 15B is an enlarged fragmentary isometric view of the fluid pathway connection assembly of FIG. 15A.
Figure 16A:
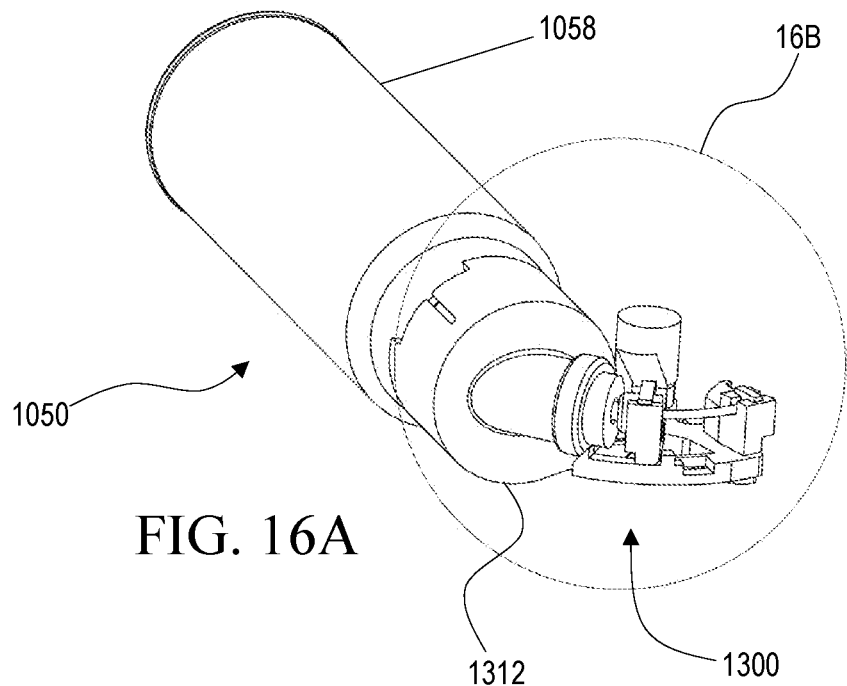
FIG. 16A is a further isometric view of the fluid pathway connection assembly and container of FIGS. 11A-11B in an actuated configuration.
Figure 16B:
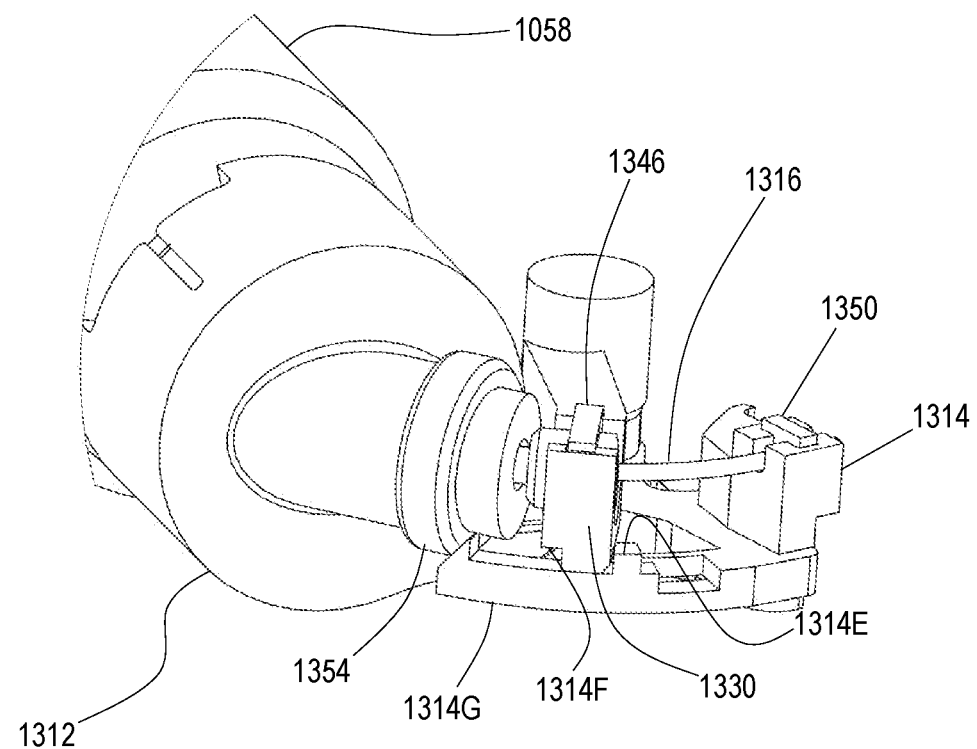
FIG. 16B is an enlarged fragmentary isometric view of the fluid pathway connection assembly of FIG. 16A.
Figure 17A:
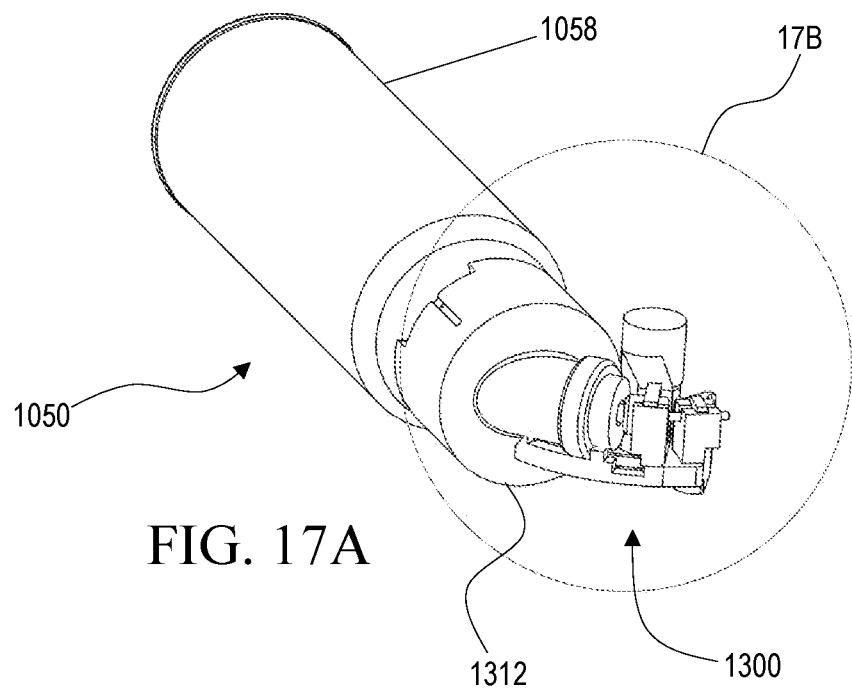
FIG. 17A is a further isometric view of the fluid pathway connection assembly and container of FIGS. 11A-11B in a delivery configuration.
Figure 17B:
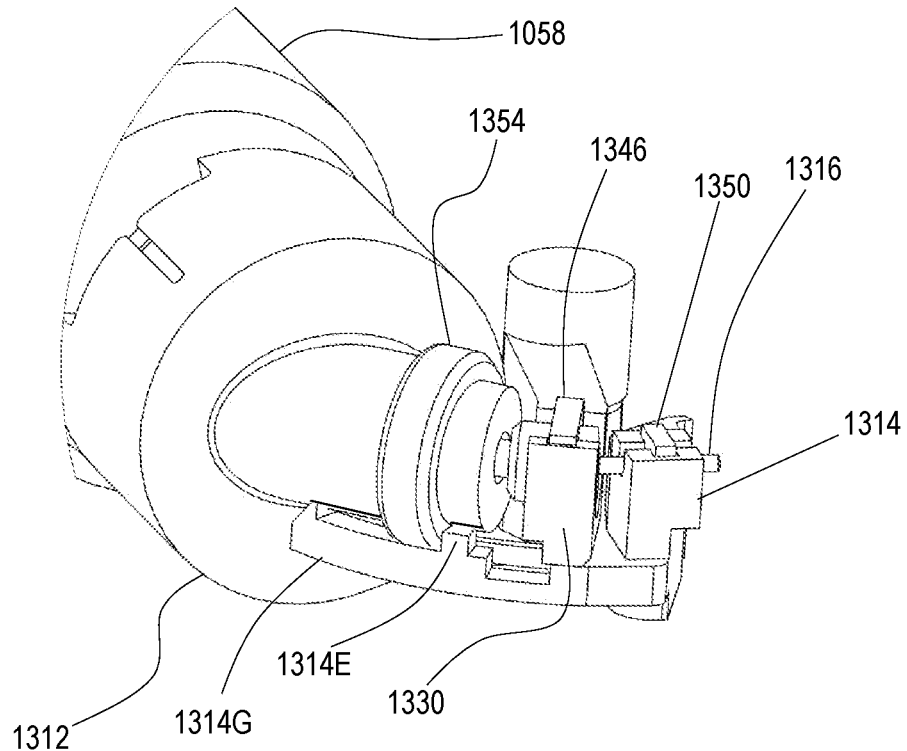
FIG. 17B is an enlarged fragmentary isometric view of the fluid pathway connection assembly of FIG. 17A.

Piercing member retainer 1314 and introducer member retainer 1330 may initially rotate as a unit. Referring to FIGS. 15B and 21, introducer member retainer 1330 may initially be disposed between projection 1314E and tooth 1314F, both features of piercing member retainer 1314. The retainers move in conjunction to the actuated configuration shown in FIGS. 13A-13B. In this position, the introducer member 1320 has pierced the first film 1318 and second film 1322, but has not pierced pierceable seal 1326. At or near to this position, flex arm 1314G of piercing member retainer 1314 contacts connection hub 1312 and/or cap 1354. Hence, continued rotation of piercing member retainer 1314 causes flex arm 1314G to be displaced downward. As a result, contact of projection 1314E with introducer member retainer 1330 no longer causes rotation of introducer member retainer 1330. Thus, further rotation of piercing member retainer 1314 does not cause additional rotation of introducer member retainer 1330.

Figure 14A:
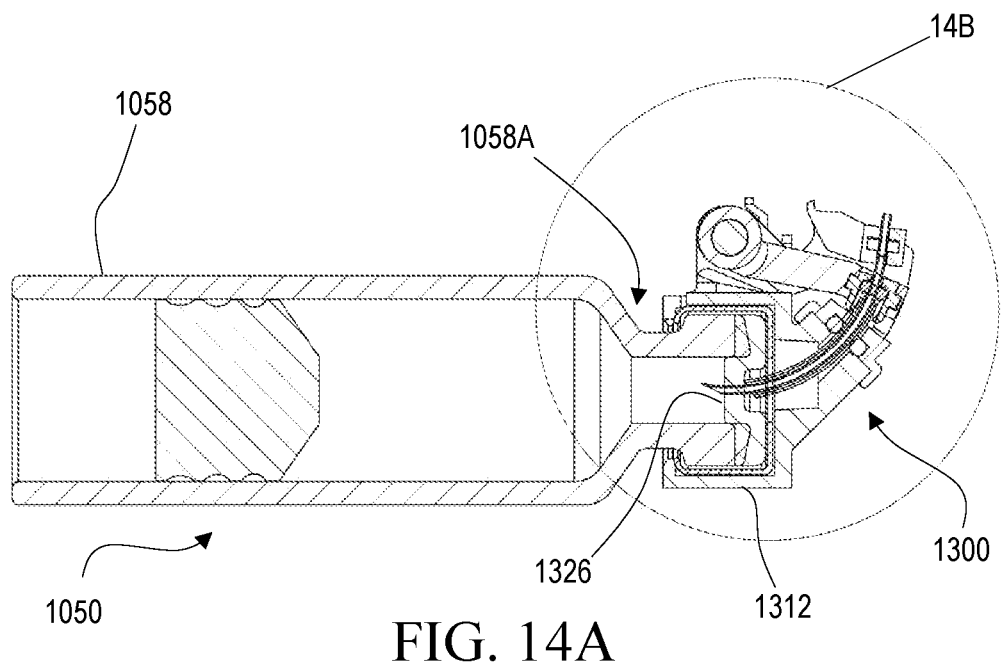
FIG. 14A is a cross-sectional side view of the embodiment of the fluid pathway connection assembly and a drug container of FIGS. 12A and 13A in a delivery configuration.
Figure 14B:
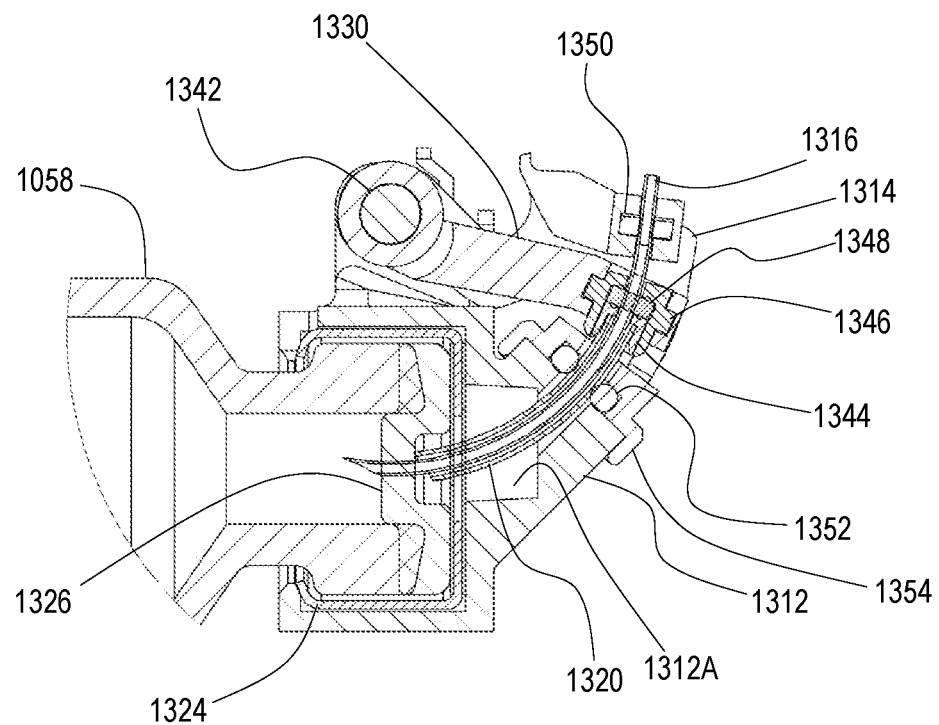
FIG. 14B is an enlarged fragmentary cross-sectional side view of the embodiment shown in FIG. 14A.
Figure 18A:
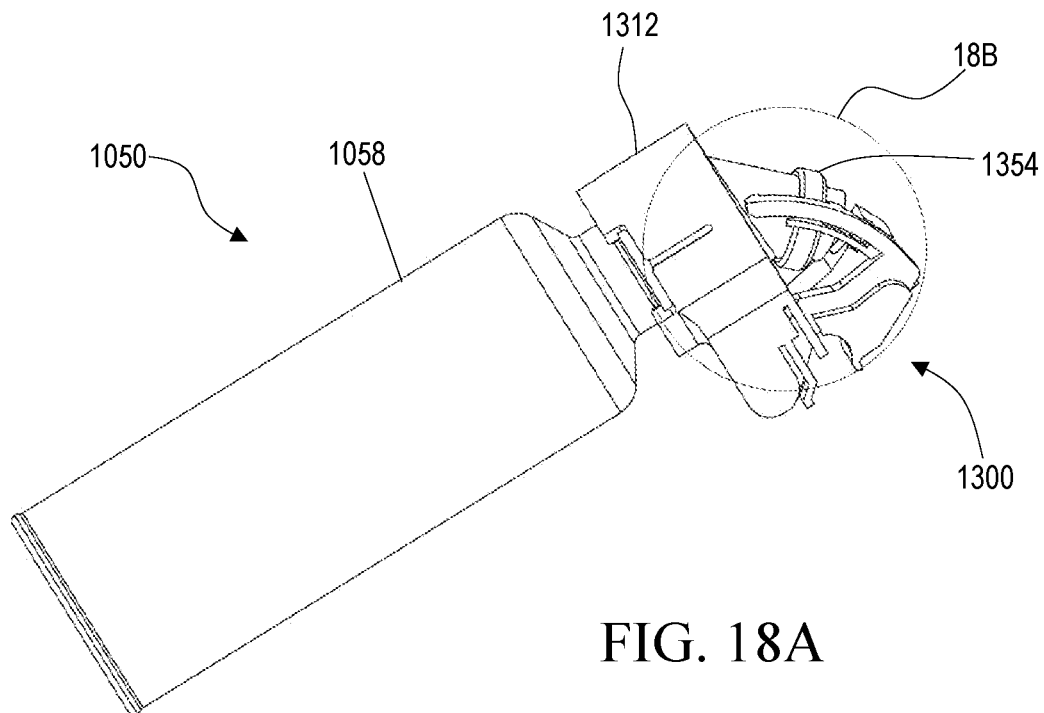
FIG. 18A is a bottom side view of the fluid pathway connection assembly and container of FIG. 17A.
Figure 18B:
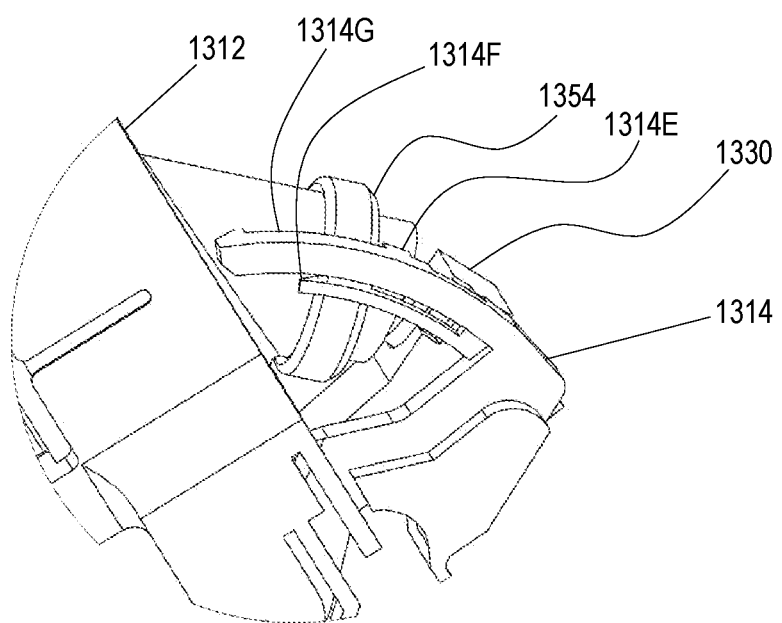
FIG. 18B is an enlarged fragmentary isometric view of the fluid pathway connection assembly and drug container of FIG. 18A.

As shown in the delivery configuration illustrated in FIGS. 14A-14B, continued rotation of piercing member retainer 1314 causes piercing member 1316 to pierce pierceable seal 1326, thus opening a flow path from the drug container 1050, through piercing member 1316. Piercing member 1316 may be in fluid communication with insertion mechanism 200, for example by a fluid conduit, to allow for delivery of the fluid drug to the patient. As shown in FIGS. 18A-18B, in this configuration, tooth 1314F may engage cap 1354 and/or connection hub 1312 to prevent retraction of piercing member 1316.

Figure 22:
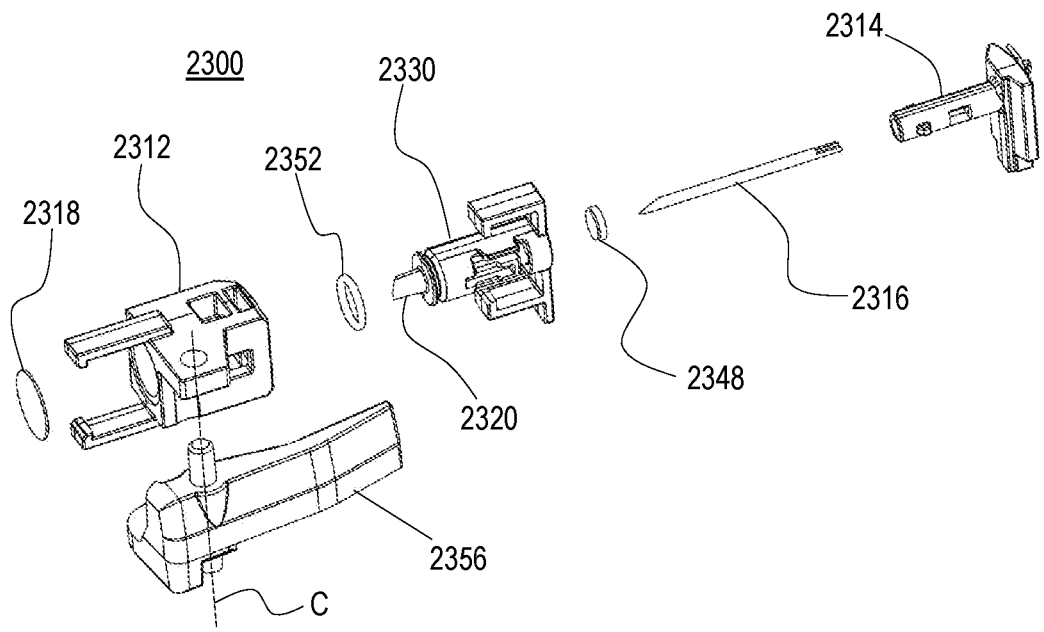
FIG. 22 shows an isometrically exploded view of a fluid pathway connection assembly according to at least one embodiment of the present invention.

FIG. 22 shows an exploded view of another embodiment of a fluid pathway connection assembly 2300. The fluid pathway connection assembly 2300 includes connection hub 2312, introducer member 2320, introducer member retainer 2330, piercing member 2316, piercing member retainer 2314, and, optionally, blocking aspect 2356. Additionally, first film 2318 may be provided such that it maintains the aseptic condition of at least a portion of the fluid pathway connection assembly. The fluid pathway connection assembly may also include ring seal 2352 and septum 2348 configured to maintain the aseptic condition of at least a portion of the fluid pathway connection assembly as described above. Blocking aspect 2356 may be configured with an interlock 2338 engaging connection hub 2312 at coupling aspect 2312H. Additionally, or alternatively, blocking aspect 2356 may be configured to engage an aspect of housing 12. Blocking aspect 2356 may be configured for rotation about these engagement points.

Figure 23A:
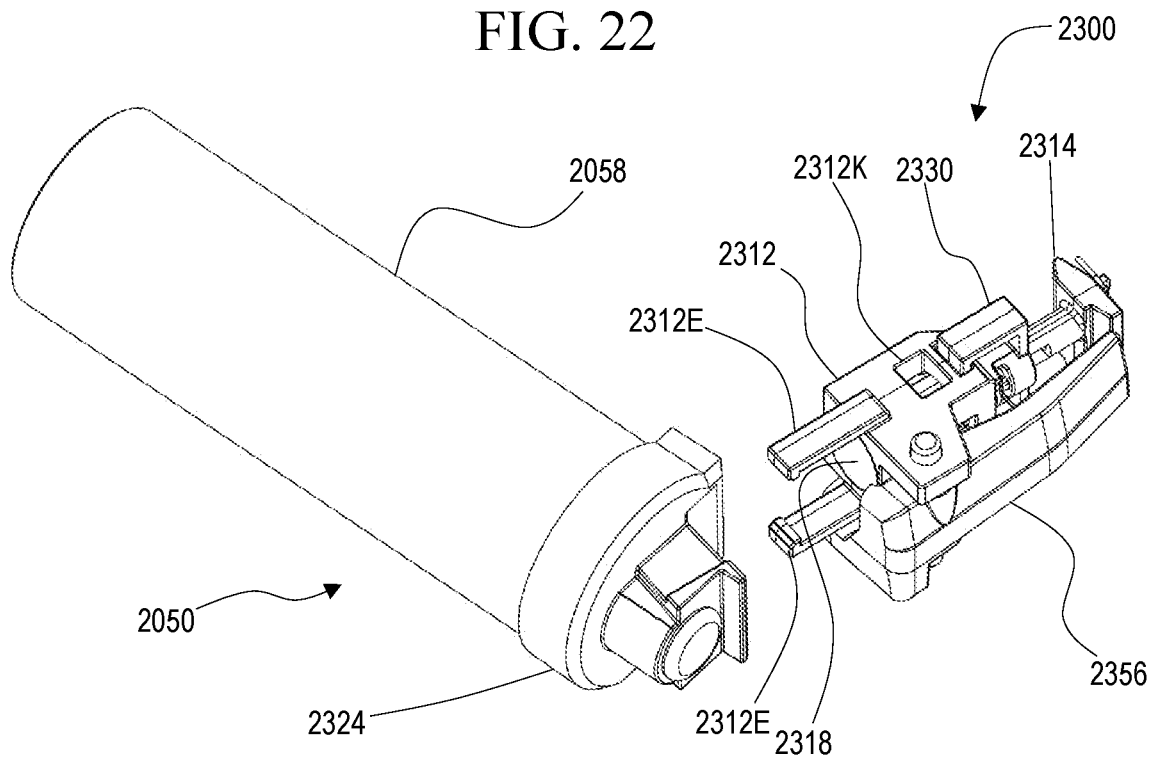
FIG. 23A shows an isometric view of the fluid pathway connection assembly and drug container of FIG. 22 in an unmounted configuration.
Figure 23B:
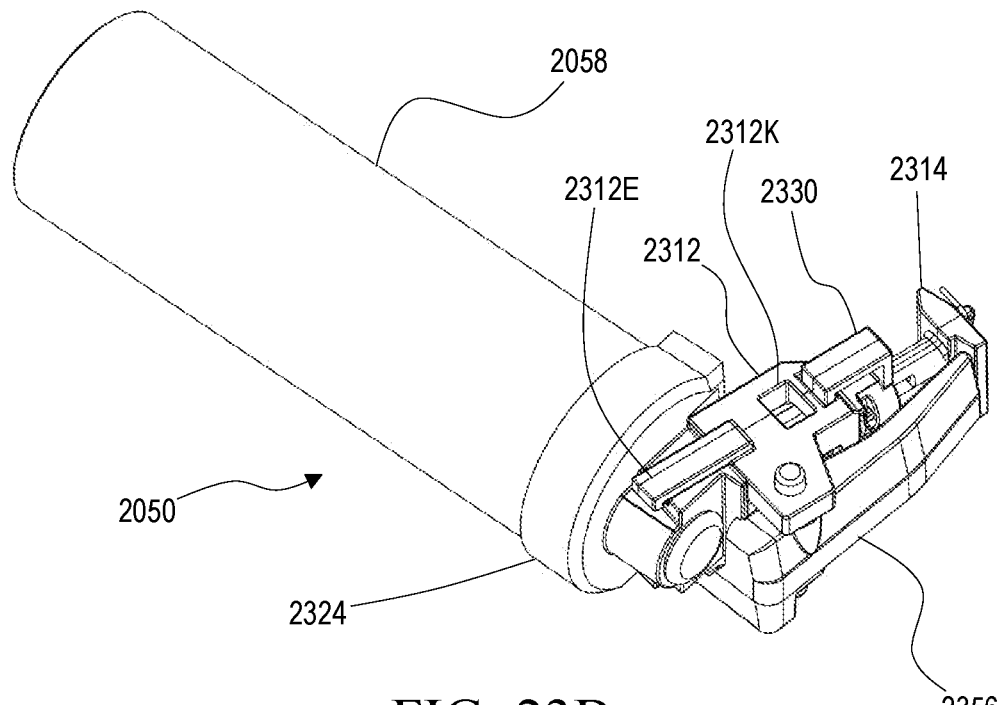
FIG. 23B is an isometric view of the fluid pathway connection assembly and drug container of FIG. 23A in a mounted, but unactuated, configuration.
Figure 23C:
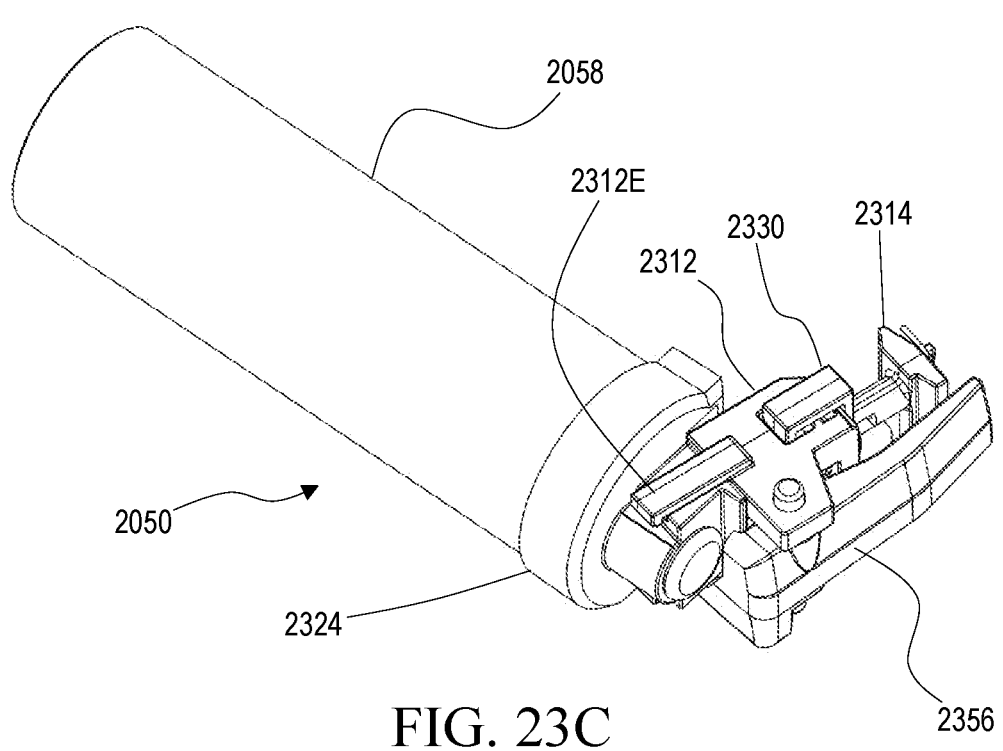
FIG. 23C is an isometric view of the fluid pathway connection assembly and drug container of FIG. 23B in an actuated configuration.
Figure 23D:
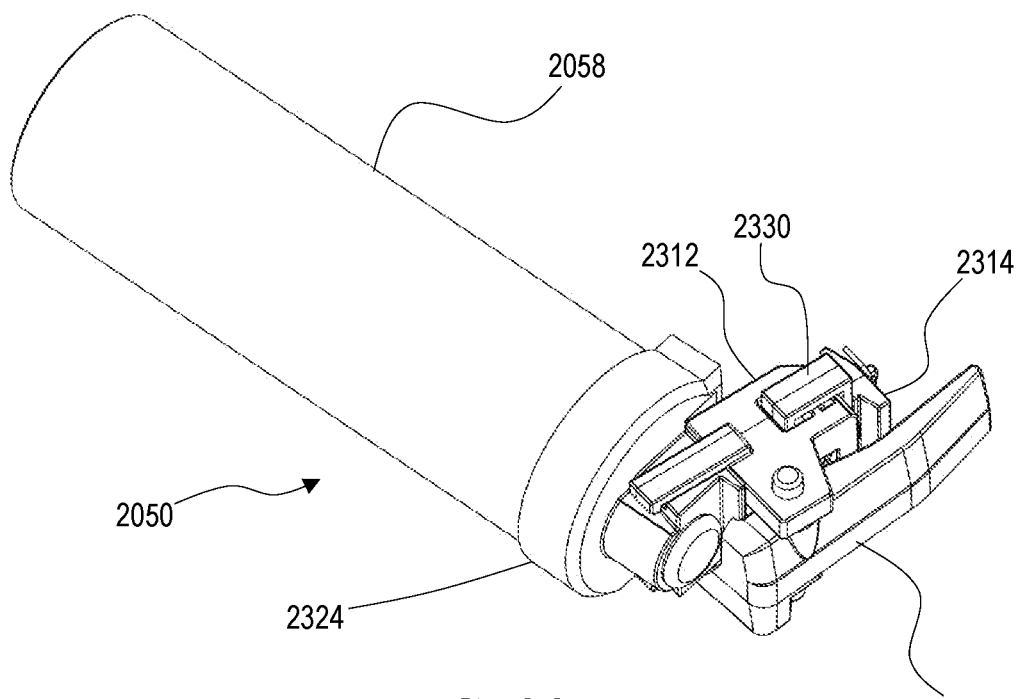
FIG. 23D is an isometric view of the fluid pathway connection assembly and drug container of FIGS. 23B-23C in a delivery configuration.

FIG. 23A shows the drug container 50 and fluid pathway connection assembly 2300 in an unactuated configuration, prior to assembly. As will be understood from the above discussion, this assembly step may take place in an uncontrolled or less controlled environment than that required for prior art designs. In order to mount the fluid pathway connection assembly 2300 to the crimp cap 2324 coupling the pierceable seal 2326 to the barrel 2058, a barrel-engaging aspect may include one or more flex arms 2312E of the connection hub 2312, which engage the pierceable seal 2326 or crimp cap 2324. FIG. 23B-23D show isometric views of the stages of operation of the fluid pathway connection assembly 2300 once mounted to the drug container 2050.

Initially, in the unactuated configuration illustrated in FIG. 23B, blocking aspect 2356 is initially engaged with piercing member retainer 2314 such that blocking aspect 2356 prevents translation of piercing member retainer 2314 toward drug container 2050. Additionally, or alternatively, one or more arms 2330E of introducer member retainer 2330 (see FIG. 28) are initially disposed in one or more primary windows 2312J of connection hub 2312 (see FIG. 27). This engagement may further prevent inadvertent activation of the fluid pathway connection assembly. For example, in at least one embodiment, arms 2330E are configured to provide sufficient flexural stiffness to resist disengagement from primary windows 2312J and prevent inadvertent activation. Application of sufficient force for activation will cause arms 2330E to disengage from primary windows 2312J, allowing translation of introducer member retainer 2330.

Figure 30:
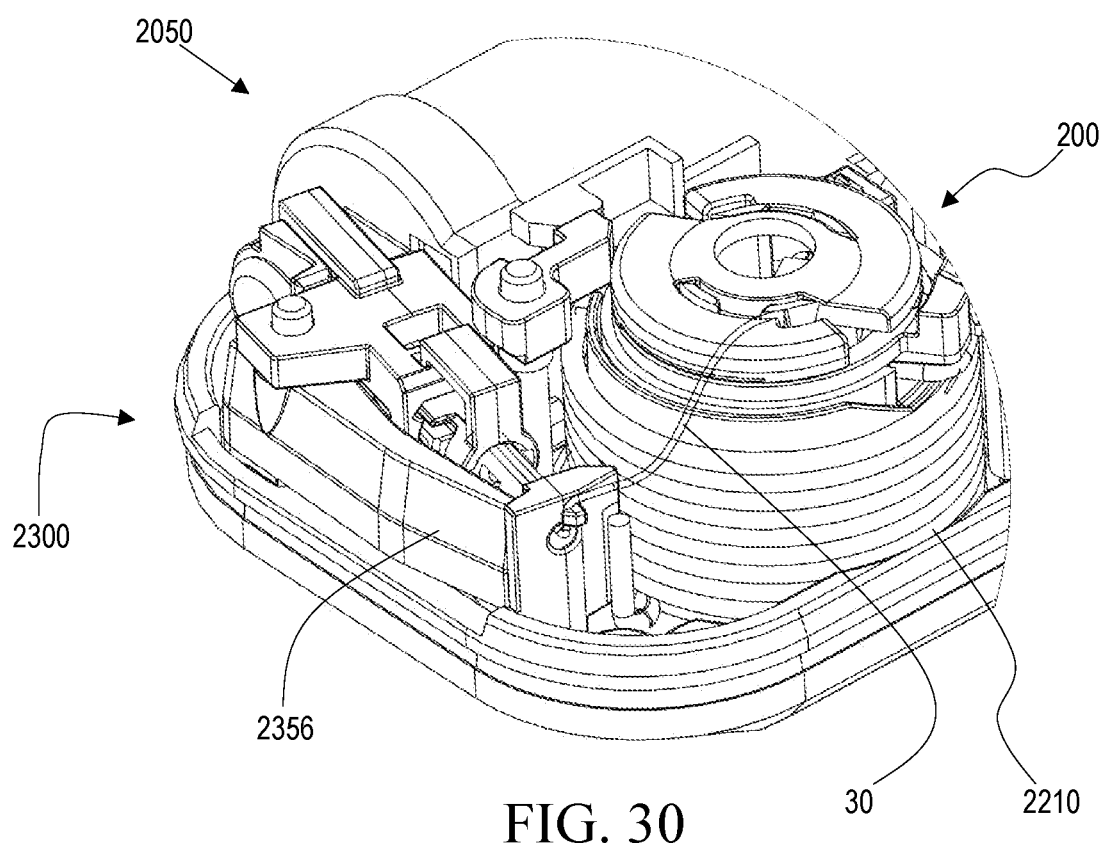
FIG. 30 shows a fragmentary isometric view of the interior components of a drug delivery pump incorporating the fluid pathway connection assembly of FIGS. 22-26B.

Upon activation, blocking aspect 2356 is displaced, for example by rotating about axis C. After displacement of blocking aspect 2356, piercing member retainer 2314 is able to translate toward drug container 2050 in response to application of a driving force from an insertion driver, such as the rotational biasing member 2210 shown in FIG. 30. FIG. 30 is a detail view showing one method of actuating the fluid pathway connection assembly 2300. As shown, rotational biasing member 2210 is initially held in a compressed or energized state. A first end of rotational biasing member 2210 is engaged with an aspect of fluid pathway connection assembly 2300, here piercing member retainer 2314. Further, a blocking aspect 2356, such as a rotatable latch, prevents de-energizing of rotational biasing member 2210 and, hence, activation of fluid pathway connection assembly 2300. To activate the fluid pathway connection assembly 2300, the blocking aspect 2356 may be displaced such that it no longer restricts de-energizing of rotational biasing member 2210. As such, upon displacement of the locking aspect 2356, rotational biasing member 2210 at least partially de-energizes and causes the fluid pathway connection assembly 2300 to open a fluid path to the drug container 2050, fluidly coupling the drug container 2050 to the needle insertion mechanism 200 via the fluid pathway connection assembly 2300 and a sterile fluid conduit 30 coupled to the piercing member 2316 and the needle insertion mechanism 200. Displacement of the blocking aspect 2356 may occur in response to depression, by the user, of activation mechanism 14 or, alternatively, may be controlled by interaction with a separate mechanism.

Returning now to FIGS. 23B-26B, initially, as is described further hereinafter, piercing member retainer 2314 and introducer member retainer 2330 move together toward drug container 2050. FIG. 23C shows the fluid pathway connection assembly in the actuated configuration, that is, after introducer member 2320 pierces first film 2318 and second film 2322. After piercing of first film 2318 and second film 2322, introducer member 2320 is restricted from further movement. In one embodiment, arms 2330E of introducer member retainer 2330 are positioned within one or more secondary windows 2312K, in this configuration. This engagement may lock the introducer member retainer in place, preventing inadvertent translation toward or away from the drug container. Continued translation of piercing member retainer 2314 causes piercing member 2316 to pierce pierceable seal 2326 to open a fluid flow path from drug container 2050. This delivery configuration is shown in FIG. 23D.

Figure 24A:
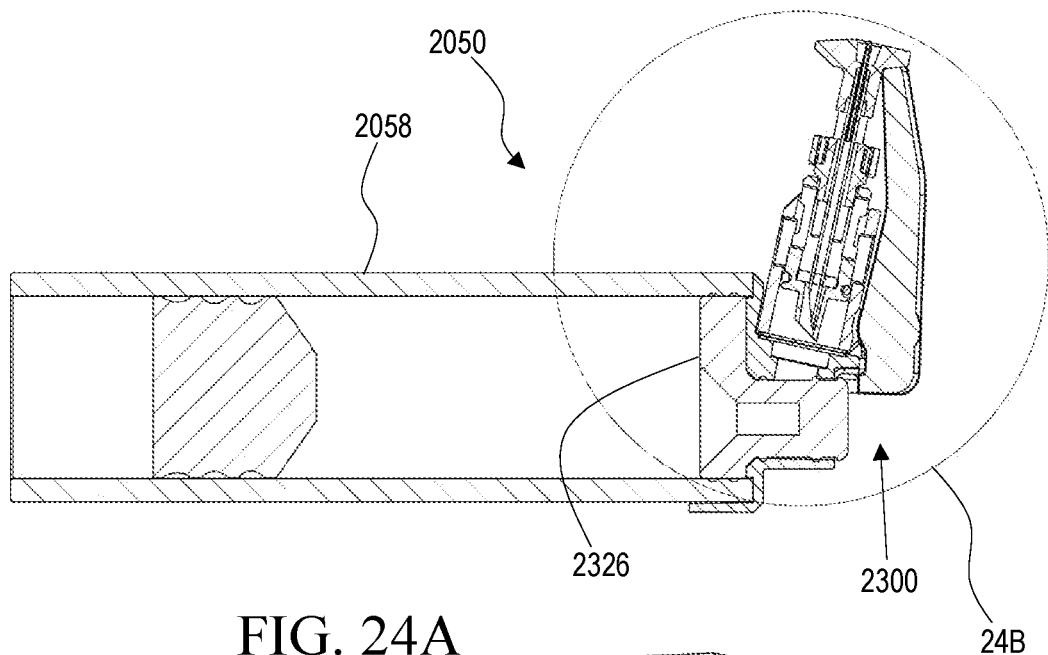
FIG. 24A is a cross-sectional side view of the fluid pathway connection assembly and drug container of FIG. 23B in the mounted, but unactuated, configuration.
Figure 24B:
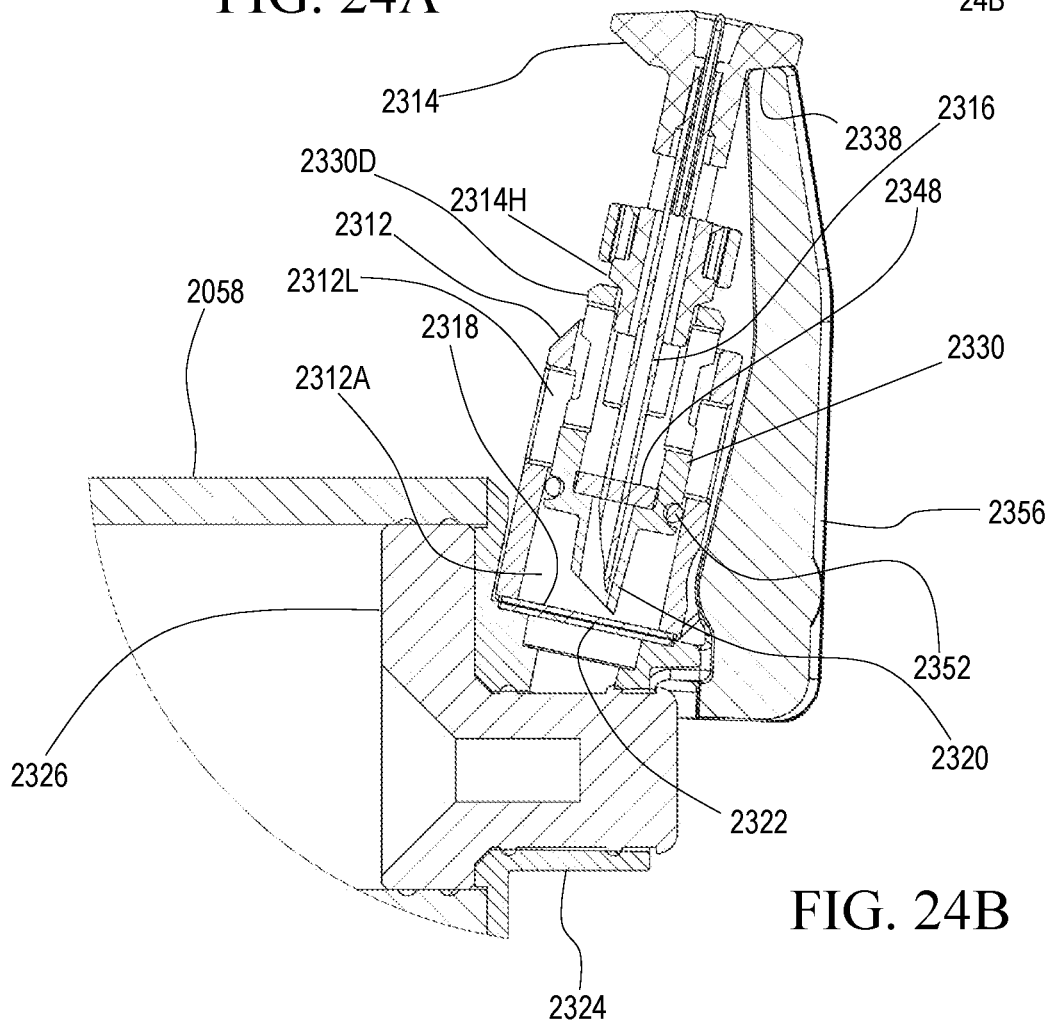
FIG. 24B is an enlarged fragmentary cross-sectional side view of the embodiment shown in FIG. 24A.

FIGS. 24A and 24B show cross-sectional views of the fluid pathway connection assembly in the initial, unactuated configuration. As can be seen in these figures, blocking aspect 2356 is engaged with piercing member retainer 2314 to prevent translation of piercing member retainer 2314 toward the drug container. Piercing member 2316 is disposed at least partially within introducer member 2320. As shown, in this or any embodiment, introducer member 2320 may be an integral portion of introducer member retainer 2330. Introducer member 2320 and piercing member 2316 are both at least partially disposed in sterile cavity 2312A, which is defined by connection hub 2312, first film 2318, ring seal 2352, and septum 2348. Shoulder 2314H of piercing member retainer 2314 is in contact with extensions 2330D of introducer member retainer 2330. Extensions 2330D are configured to be relatively flexible aspects of introducer member retainer 2330. However, in the initial configuration, extensions 2330D are prevented from flexing by contact with connection hub 2312. Hence, initially, translation of piercing member retainer 2314, toward drug container 2050, causes commensurate translation of piercing member retainer 2314.

Figure 25A:
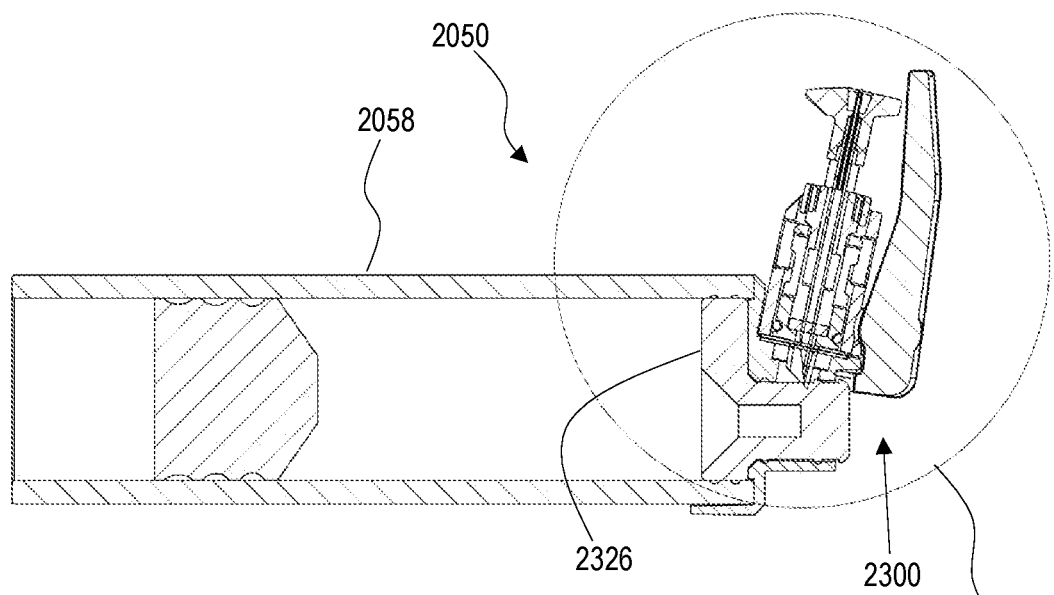
FIG. 25A is a cross-sectional side view of the embodiment of the fluid pathway connection assembly and drug container of FIG. 23B in an actuated configuration.
Figure 25B:
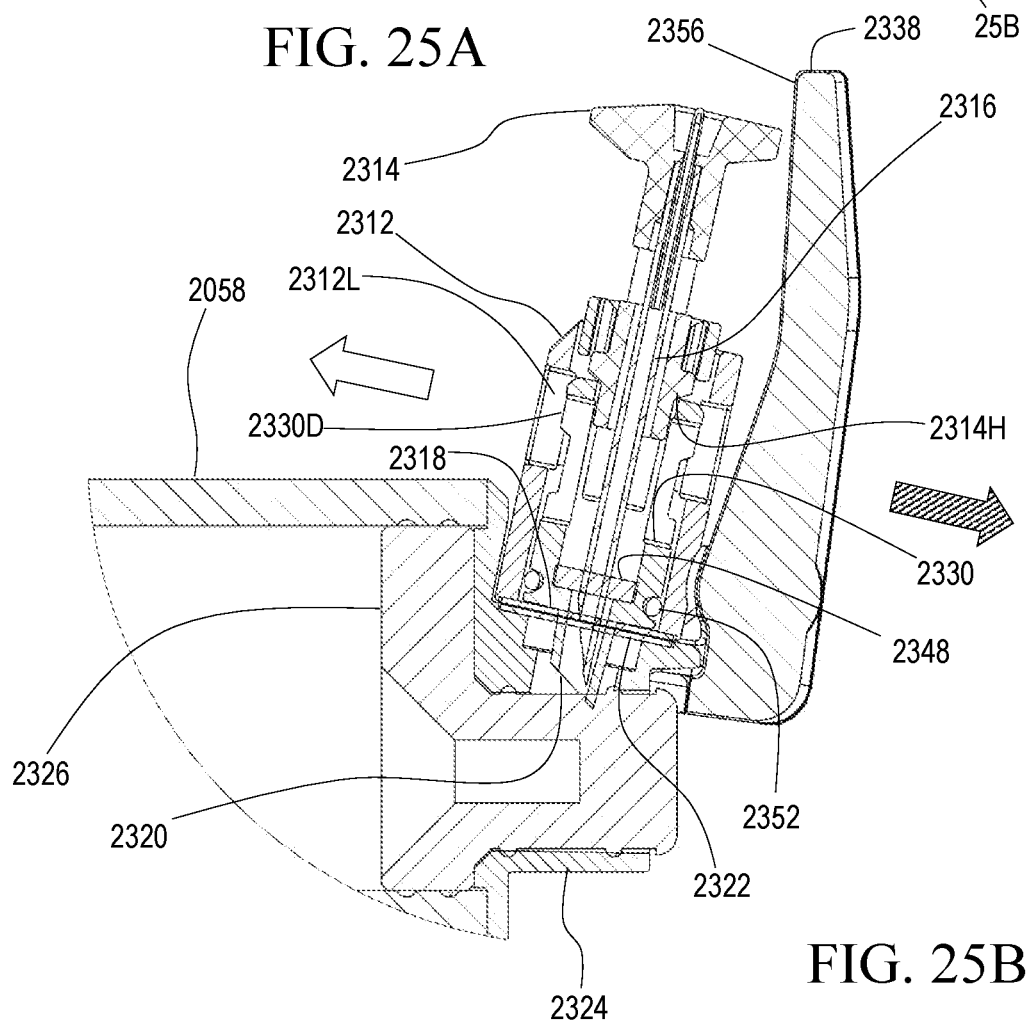
FIG. 25B is an enlarged fragmentary cross-sectional side view of the embodiment shown in FIG. 25A.
Figure 26A:
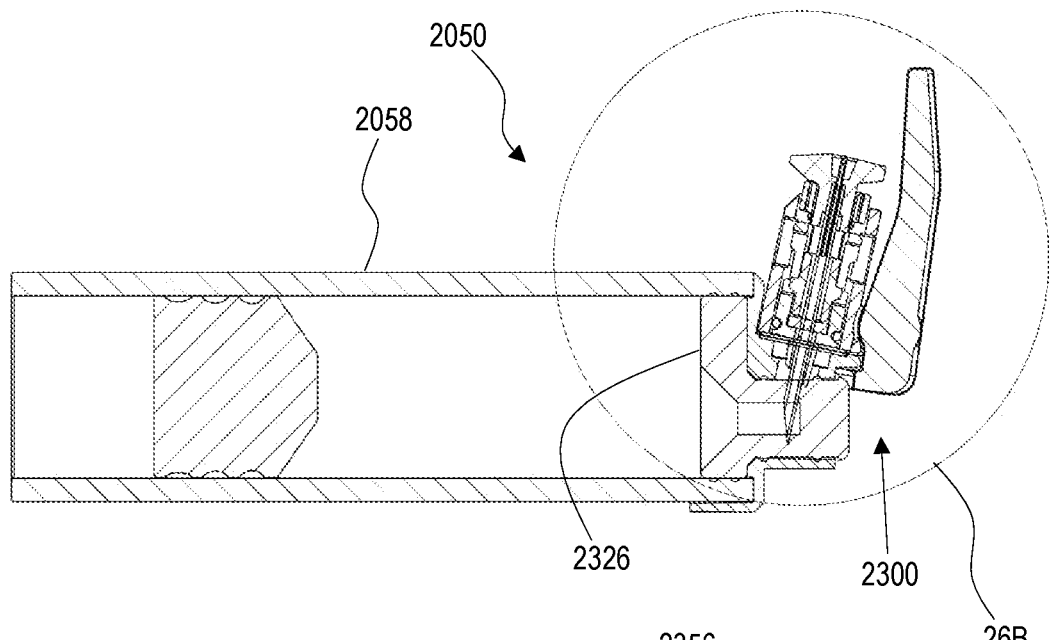
FIG. 26A is a cross-sectional side view of the embodiment of the fluid pathway connection assembly and drug container of FIGS. 24A and 25A in a delivery configuration.
Figure 26B:
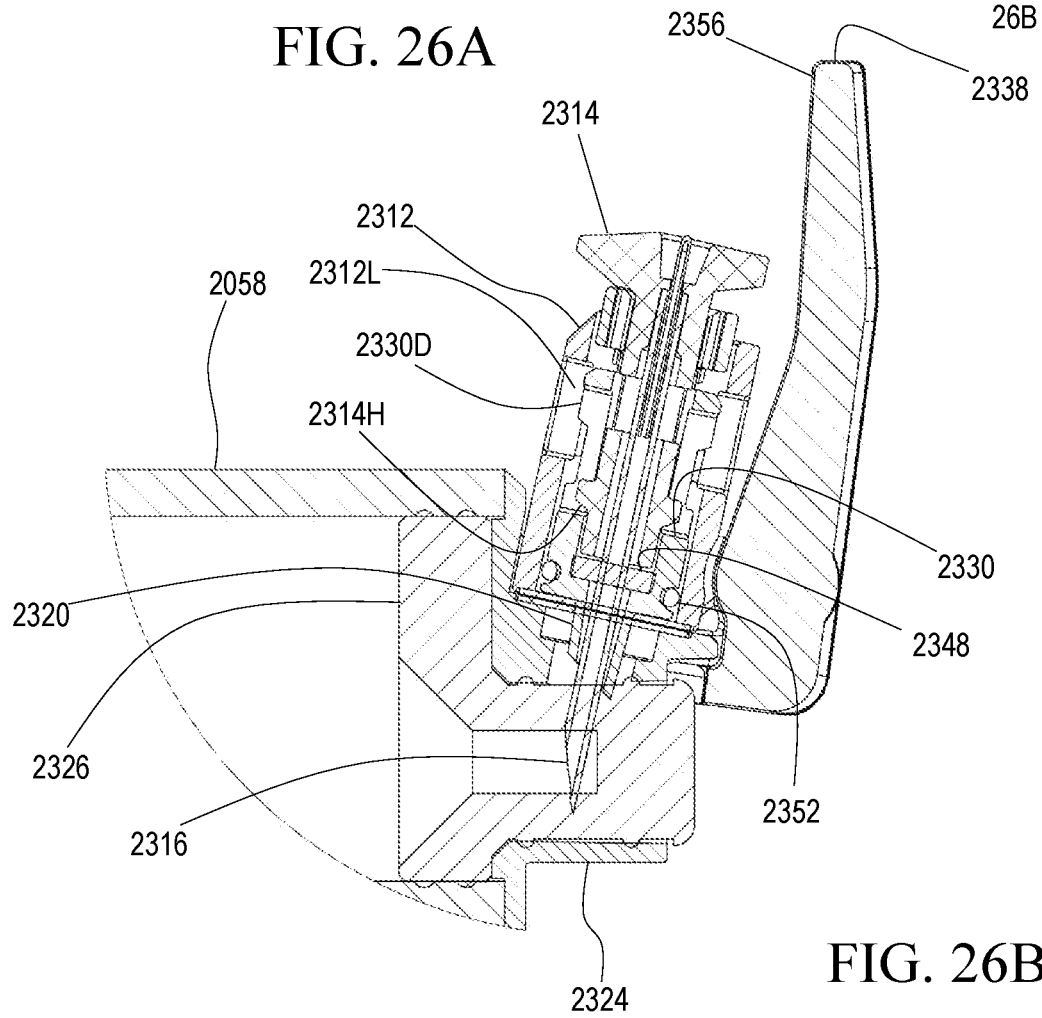
FIG. 26B is an enlarged fragmentary cross-sectional side view of the embodiment shown in FIG. 26A.
Figure 27:
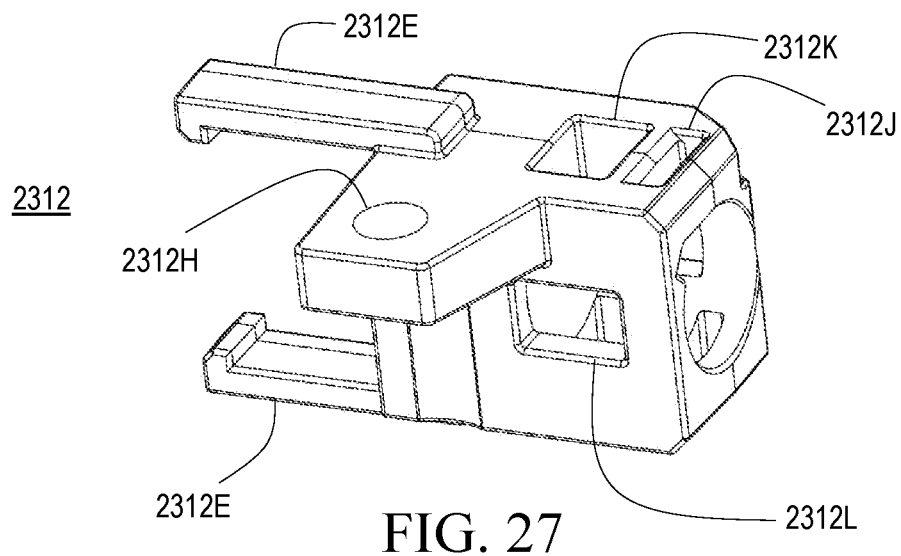
FIG. 27 shows an isometric view of a connection hub according to at least one embodiment of the present invention.
Figure 28:
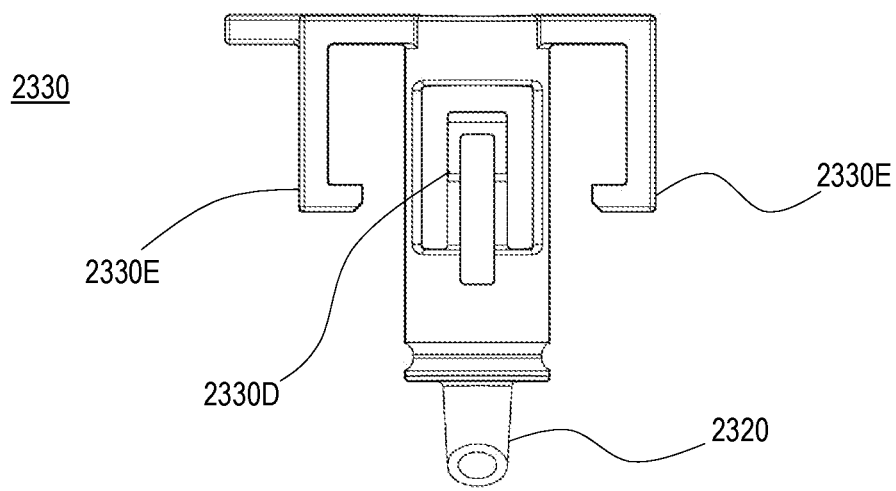
FIG. 28 shows a side elevational view of an embodiment of an introducer member retainer according to at least one embodiment of the present invention.
Figure 29:
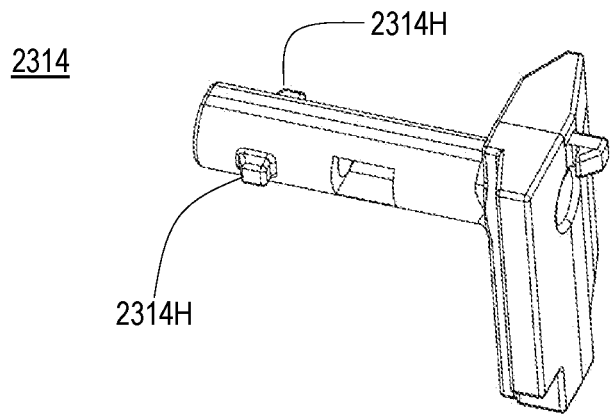
FIG. 29 shows an isometric view of an embodiment of a piercing member retainer according to at least one embodiment of the present invention.

FIGS. 25A-25B show the fluid pathway connection assembly 2300 in an intermediate, actuated configuration. In this configuration, blocking aspect 2356 has been displaced such that it does not restrict translation of piercing member retainer 2314. Introducer member 2320 has pierced first film 2318 and second film 2322 and piercing member 2316 is positioned adjacent to pierceable seal 2326. Also, in this configuration, extensions 2330D are positioned adjacent to recesses 2312L of connection hub 2312. Hence, extensions 2330D are no longer restricted from flexing outward (i.e., in the direction of the hatched arrows in FIG. 25B). Because extensions 2330D are able to flex outward, into recesses 2312L, additional translation of piercing member retainer 2314 causes shoulders 2314H to disengage from extensions 2330D. This allows piercing member retainer 2314 to translate toward drug container 2050 without causing translation of introducer member retainer 2330. As shown in the delivery configuration of FIGS. 26A-26B, this allows piercing member 2316 to pierce pierceable seal 2326 and open the fluid flow path from the drug container 2050.

In some embodiments, an additional film or seal may be present at the tip of introducer member 320, 1320, 2320 sealing the lumen of the introducer member and, thereby, further isolating the lumen of the introducer member and, hence, the piercing member in order to maintain the aseptic condition of the piercing member. This film may remain intact as the introducer member pierces first film 318, 1318, 2318 and second film 322, 1322, 2322. This may further prevent any microbes or other contaminants that are present on the surfaces of the seals from coming in contact with the piercing member.

In at least one other embodiment, the first and second films are removed from the fluid pathway connection assembly and drug container just prior to mounting of the fluid pathway connection assembly 300 to the drug container 50. Prior to removal of the films, their placement maintains the sterility of the pierceable seal of the drug container and cavity 312A. Connection hub 312 and drug container 50 may be configured such that connection of the connection hub to the barrel provides a sealing engagement to maintain the aseptic condition of the pierceable seal and piercing member. In such an embodiment, connection hub 312 and/or drug container 50 may include an elastomeric aspect which is configured to provide sealing engagement.

In another embodiment, after mounting of connection hub 312 to drug container 50, the cavity 312A and pierceable seal 326 may be sterilized using UV sterilization. The connection hub 312 may be in sealing engagement with the drug container such that after sterilization microbes and other foreign elements are unable to contact the aseptic surfaces. In such embodiments, at least a portion of the connection hub may be constructed from a substantially translucent material, such as glass.

In each of the embodiments described herein, the connection hub, piercing member retainer, and/or the introducer member retainer may include one or more features to prevent the inadvertent activation of the fluid pathway connection assembly during assembly, storage, transportation, and handling. These features may prevent activation unless a force above a threshold value is applied. These features may, for example, include flexible aspects or frangible aspects which are displaced or severed upon application of a force above the threshold.

In addition to the advantages described above, the insertion mechanisms described herein may also be capable of terminating flow of medicament to the target tissue by disconnecting the fluid path. This may be an important safety feature to protect the patient. For example, some medicaments, such as insulin, can be dangerous, and potentially even deadly, when administered in too large a quantity and/or at too rapid of a rate. By providing such automatic safety stop mechanisms, so-called "run-away" delivery of medicament may be prevented, thereby ensuring the safety of the patient. While the methods and associated structures for terminating flow may be discussed with regard to one or more specific insertion mechanisms disclosed herein, it will be appreciated that the method and associated structures may be utilized or adapted for any of the fluid pathway connection assemblies disclosed herein or within the spirit and scope of this disclosure.

An interruption in delivery of medicament through the fluid pathway connection assembly may be triggered, for example, by an error in delivery of the medicament or by an input from the user. For example, the user may realize that they have already taken their drug dose and wish to pause or terminate drug delivery from the device. Upon such user input to the device, the delivery of the drug can be stopped and/or the fluid passageway through the piercing member may be terminated by retraction of the piercing member to a retracted position, as described below.

Additionally or alternatively, the device may pause or terminate drug delivery if it receives an error alert during operation. For example, if the drive mechanism is not functioning correctly, the fluid pathway connection assembly may be triggered to retract the piercing member from the pierceable seal to terminate drug delivery through the fluid pathway connection assembly to prevent over-delivery of a medication. This capability of the fluid pathway connection assembly provides a valuable safety feature for drug delivery to a target.

In some embodiments, retraction is activated upon removal of the drug pump from the target tissue. In other embodiments, retraction is activated if it is determined that an error has occurred in the delivery of the substances to the target tissue. For example, an occlusion of the drug delivery pathway which prevents the flow of medicament may be detected by a sensing function of the drug delivery pump. Upon the sensing of the occlusion an electrical or mechanical input may be used to initiate retraction of the needle.

Additionally or alternatively, one or more biasing members may be included to disconnect the fluid pathway connection assembly. This may provide a desirable safety feature, to disconnect the fluid pathway upon signaling of an error condition either automatically by the drug delivery pump or upon action by the user. For example, a locking aspect may initially restrain a secondary biasing member from expanding from its original energized state. Upon activation of the locking aspect, the secondary biasing member is caused to de-energize from its original position and, thereby, act upon and axially translate the piercing member retainer to disconnect the piercing member from the pierceable seal. Once the fluid pathway connection assembly is disconnected, flow of drug fluid is restricted or blocked between the drug container and the fluid conduit to limit or prevent fluid flow to the needle insertion mechanism and into the target. As described herein, the disconnection may be triggered by a number of operations, automatically by the system and/or upon direct or indirect user initiation, as an added safety precaution to prevent over-delivery of the drug fluid to the target.

Figure 31A:
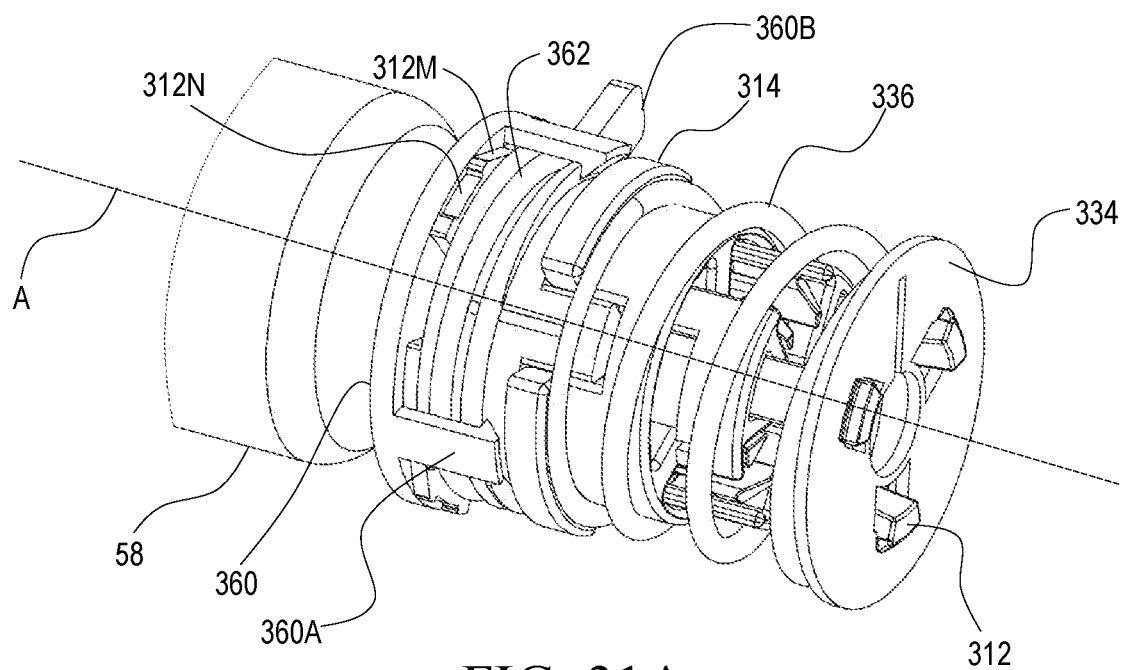
FIG. 31A is a fragmentary isometric view of a fluid pathway connection assembly and a drug container of at least one embodiment of the present invention during fluid connection.
Figure 31B:
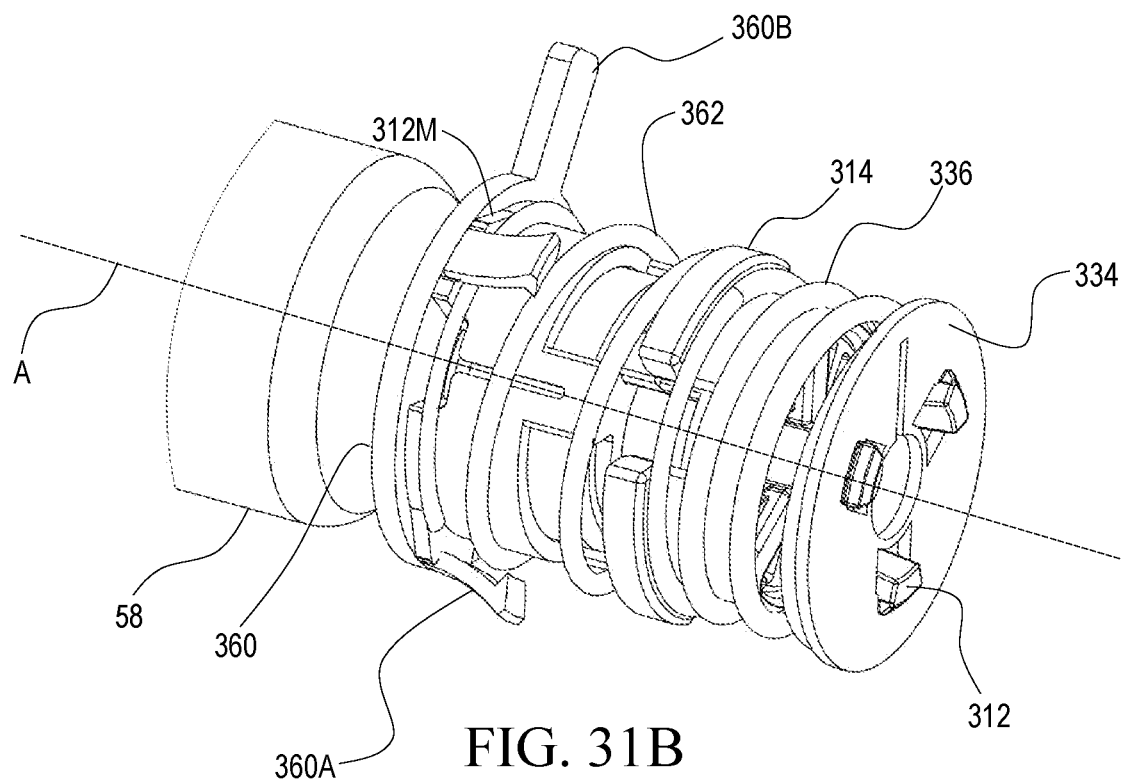
FIG. 31B is a fragmentary isometric view of the fluid pathway connection assembly and drug container of FIG. 31A upon disconnection.

One such embodiment is shown in FIGS. 31A and 31B. As shown in FIG. 31A, secondary biasing member 362 is initially restrained between connection hub 312 and one or more release arms 360A of locking aspect 360. Locking aspect 360 is disposed against the proximal face of connection hub 312 with one or more release arms extending in the distal direction. In the event of a fault in the operation of the drug pump, or upon activation by the user, locking aspect 360 is caused to rotate about axis A from the position shown in FIG. 31A to the position shown in FIG. 31B. The rotation may be caused by contact of a throw arm with activation arm 360B, for example. As locking aspect 360 is rotated, each of the one or more release arms 360A contact a ramped surface 312M of connection hub 312. The contact with ramped surface 312M causes displacement of the one or more release arms 360A in an outwardly radial direction or, alternatively, fracture of the one or more release arms 360A. As a result, secondary biasing member 362 is able to decompress or deenergize. Secondary biasing member 362 comes into contact with piercing member retainer 314 and causes piercing member retainer 314 to translate in the distal direction. This translation causes the piercing member to be withdrawn from the pierceable seal. Hence, no additional medicament will be delivered through the piercing member, thereby terminating delivery to the patient. As shown in FIG. 31B, after rotation, each of the one or more release arms 360A may flex radially outward to permit the secondary biasing member 362 to deenergize, and then return radially inward to be disposed in a notch 312N of the connection hub. Locking aspect 360 may thereby be prevented from any further rotation.

Any of the illustrated embodiments may be equipped with such a safety feature. Alternatively, a component of the drug pump may directly engage a portion of the fluid pathway connection assembly to withdraw the piercing member from the pierceable seal. For example, a slide or throw arm may contact piercing member retainer 2314, displacement of the slide or throw arm causing displacement of piercing member retainer 2314 to withdraw the piercing member from the pierceable seal.

Withdrawal of the piercing member from the pierceable seal may be activated in the event of, for example, failure or loss of tension in the tether, failure of the drive mechanism, removal of the drug pump from the target tissue, or activation by the user. The safety mechanism may be purely mechanical or, alternatively, may include the power and control system. For example, an electrical signal from the power and control system may initiate withdrawal of the piercing member from the pierceable seal.

It will be appreciated from the above description that the fluid pathway connection assemblies and drug pumps disclosed herein provide an efficient and easily-operated system for automated drug delivery from a drug container. The novel devices of the present disclosure provide container connections maintain the aseptic condition of the fluid pathway, and drug delivery pumps which incorporate such fluid pathway connection assemblies to drug containers. Such devices are safe and easy to use, and are aesthetically and ergonomically appealing for self-administering patients. The devices described herein incorporate features which make activation, operation, and lock-out of the device simple for even untrained users. Because the fluid path is disconnected until drug delivery is desired by the user, the aseptic condition of the fluid pathway connection assembly, the drug container, the drug fluid, and the device as a whole is maintained. These aspects provide highly desirable storage, transportation, and safety advantages to the user. Furthermore, the novel configurations of the fluid pathway connection assemblies and drug pumps of the present disclosure maintain the aseptic condition of the fluid path throughout operation of the device. Because the path that the drug fluid travels within the device is entirely maintained in an aseptic condition, only these components need be sterilized during the manufacturing process. Such components include the drug container of the drive mechanism, the fluid pathway connection assembly, the sterile fluid conduit, and the insertion mechanism. In at least one embodiment, the power and control system, the assembly platform, the activation mechanism, the housing, and other components of the drug pump do not need to be sterilized. This greatly improves the manufacturability of the device and reduces associated assembly costs. Accordingly, the devices of the present invention do not require terminal sterilization upon completion of assembly. A further benefit is that the components described herein are designed to be modular such that, for example, housing and other components of the pump drug may readily be configured to accept and operate connection hub 312, 1312, 2312, or a number of other variations of the components described herein.

Assembly and/or manufacturing of fluid pathway connection assembly 300, 1300, 2300, drug delivery pump 10, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

The fluid pathway connection assembly and drug container may be assembled in a number of methodologies. In one method of assembly, the drug container 50 may be assembled and filled with a fluid for delivery to the target. The drug container 50 includes a cap 324, a pierceable seal 326, a barrel 58, and a plunger seal 60. The plunger seal 60 may be inserted into barrel 58. The barrel 58 may be filled with a drug fluid through the open distal end prior to insertion of the pierceable seal at the open distal end of the barrel 58. The pierceable seal 326 may then be fixedly engaged between the cap 324 and the barrel 58, at a distal end of the barrel 58. In this way, the drug container can be filled and sealed using standard fill-finish processes and equipment. For example, drug container 50 may be filled and sealed using processes and equipment commonly employed in the filling and sealing of standard vials. Additionally, cap 324 may be a crimp cap similar to those commonly used in such processes. Before or after applying cap 324, second seal or film 322 may be applied to the distal face of drug container 50.

Piercing member 316 may be fixedly engaged with piercing member retainer 314. Shaft 314A of piercing member retainer 314 may be inserted through central bore 334B of plate 334 and interlock 338 may engage piercing member retainer 314 such that biasing member 336 is prevented from decompressing. Introducer member 320 may be fixedly connected to introducer member retainer 330. Additionally, sterile boot 340 may be connected to introducer member retainer 330. Introducer member retainer 330 may be positioned within piercing member retainer 314 such that piercing member 316 is at least partially disposed within lumen 320A of introducer member 320. Connection hub 312 may then be connected to plate 334 by inserting snaps 312C through passages 334A. In this position, a portion of introducer member 320 is disposed within cavity 312A and sterile boot 340 is engaged with connection hub 312. Second film 322 may be placed over aperture 312B of connection hub 312 to define cavity 312A. Additionally, during assembly, the fluid conduit may be fluidly connected to piercing member 316. The insertion mechanism 200 may be assembled and attached to the other end of the fluid conduit. The fluid pathway connection assembly may then be assembled to drug container 50. The connection of the fluid pathway connection assembly to the drug container may or may not occur in a clean room or sterile environment. Because first film 318 and second film 322 maintain the aseptic condition of pierceable seal 326 and cavity 312A, respectively, the flow path is not exposed to contaminants.

The steps of assembly may, optionally, also include the step of disposing a locking aspect against the proximal face of the connection hub. The steps of assembly may also include disposing a secondary biasing member concentrically around a portion of the connection hub such that the secondary biasing member is retained in a compressed or energized state by the locking aspect.

In the embodiment shown in FIGS. 11A-21, assembly may include the steps outlined above and may also include additional or different steps. The additional or different steps may include connection of cap 1354 to connection hub 1312 such that ring seal 1352 is positioned between connection hub 1312 and cap 1354. The additional or different steps may also include placing piercing member retainer 1314 and introducer member retainer 1330 on shaft 1342 such that they are able to rotate about shaft 1342. Additionally, the steps may include fixedly engaging introducer member 1320 to first sleeve 1344 and engaging first sleeve 1344 to second sleeve 1346 such that septum 1348 is positioned between the sleeves. The steps may also include fixedly engaging piercing member 1316 to keeper 1350.

The embodiment shown in FIGS. 22-29 may also be assembled using any of the steps outlined above and may also include additional or different steps. The additional or different steps may include, for example, coupling a blocking aspect with the connection hub at a coupling aspect of the connection hub.

The drive mechanism 100 may be attached to the proximal end of the drug container 50. Certain components of this sub-assembly may be mounted to the assembly platform 20 or directly to the interior of the housing 12, while other components are mounted to the guide 390 for activation by the user.

Manufacturing of a drug pump includes the step of attaching both the fluid pathway connection assembly and drug container, either separately or as a combined component, to an assembly platform or housing of the drug pump. The method of manufacturing further includes attachment of the drive mechanism, drug container, and insertion mechanism to the assembly platform or housing. The additional components of the drug pump, as described above, including the power and control system, the activation mechanism, and the control arm may be attached, preformed, or pre-assembled to the assembly platform or housing. An adhesive patch and patch liner may be attached to the housing surface of the drug pump that contacts the target during operation of the device.

A method of operating the drug pump includes the steps of: activating, by a user, the activation mechanism; displacing a control arm to actuate an insertion mechanism; actuating a fluid pathway connection assembly; and actuating a power and control system to activate a drive control mechanism to drive fluid drug flow through the drug pump, wherein actuating the fluid pathway connection assembly causes a piercing member to penetrate a pierceable seal thereby opening a fluid path from a drug container to the fluid pathway connection assembly. The method may further include the step of: engaging an optional on-body sensor prior to activating the activation mechanism. Furthermore, the method of operation may include translating a plunger seal within the drive control mechanism and drug container to force fluid drug flow through the drug container, the fluid pathway connection assembly, a sterile fluid conduit, and the insertion mechanism for delivery of the fluid drug to the target.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

We claim as our invention:

1. A fluid pathway connection assembly for use with a drug container in a drug delivery pump, the drug container including a barrel, a cap and a pierceable seal, the fluid pathway connection assembly including an unactuated configuration, an actuated configuration, and a delivery configuration, the fluid pathway connection assembly comprising:
   a connection hub including an aperture,
   a first film sealed along the aperture, the connection hub including a sterile cavity sealed by the first film,
   an introducer member at least partially disposed within the sterile cavity in the unactuated configuration,
   a piercing member configured to telescope from the introducer member, the piercing member including a piercing tip at least partially disposed within the introducer member in the unactuated configuration,
   a piercing member retainer connected to the piercing member,
   the introducer member being configured to move relative to the connection hub from the unactuated configuration to the actuated configuration in which the introducer member pierces the first film, and
   the piercing member being configured to telescope from the introducer member to move from the unactuated configuration to the delivery configuration in which the piercing tip is not disposed within the introducer member, the piercing member being adapted to pierce the pierceable seal in the delivery configuration, the piercing member providing a fluid pathway through the pierceable seal in the delivery configuration.

2. The fluid pathway connection assembly of claim 1 further including an insertion driver disposed to move at least one of the introducer member and the piercing member from the unactuated configuration to at least one of the actuated configuration and the delivery configuration.

3. The fluid pathway connection assembly of claim 2 wherein the insertion driver includes a rotational biasing member.

4. The fluid pathway connection assembly of claim 2 wherein the insertion driver includes at least one of a torsion spring, a compression spring, or a tension spring.

5. The fluid pathway connection assembly of claim 1 further including a sterile boot, the sterile boot further defining the sterile cavity within the connection hub.

6. The fluid pathway connection assembly of claim 1 wherein the introducer member and the piercing member are configured to move linearly between the unactuated, actuated, and delivery configurations.

7. The fluid pathway connection assembly of claim 6 wherein the introducer member, the piercing member, and the drug container are linearly disposed along an axis.

8. The fluid pathway connection assembly of claim 6 wherein an axis including the introducer member and the piercing member is disposed in an angle other than parallel to an axis of the drug container.

9. The fluid pathway connection assembly of claim 1 wherein the introducer member and the piercing member are configured to move arcuately between the unactuated, actuated, and delivery configurations.

10. The fluid pathway connection assembly of claim 9 further including an introducer member retainer that pivots about an axis between the unactuated and actuated configurations, and wherein the piercing member retainer pivots about the axis between the unactuated and delivery configurations.

11. The fluid pathway connection assembly of claim 1 further including an interlock disposed to engage the piercing member retainer to prevent movement of the piercing member in the unactuated configuration.

12. The fluid pathway connection assembly of claim 1 wherein the introducer member is configured to pierce the first film upon engagement of the fluid pathway connection assembly with the drug container to move the fluid pathway connection assembly to the actuated configuration.

13. The fluid pathway connection assembly of claim 1 configured to move the piercing member from the delivery configuration to a retracted configuration wherein the piercing member is disengaged from the pierceable seal in response to a termination mechanism.

14. The fluid pathway connection assembly of claim 13 wherein the piercing tip of the piercing member is disposed within the introducer member in the retracted configuration.

15. The fluid pathway connection assembly of claim 13 further including a retraction biasing member disposed to move the piercing member from the delivery configuration to the retracted configuration.

16. The fluid pathway connection assembly of claim 13, wherein the termination mechanism is at least one of a removal of the drug pump from a target, a fault in a drive mechanism, or a failure of a tether of the drive mechanism.

17. An assembly comprising:
a drug container including a barrel, a cap, and a pierceable seal; and
a fluid pathway connection assembly including
a connection hub including an aperture,
a first film sealed along the aperture, the connection hub including a sterile cavity sealed by the first film,
an introducer member at least partially disposed within the sterile cavity in an unactuated configuration,
a piercing member configured to telescope from the introducer member, the piercing member including a piercing tip at least partially disposed within the introducer member in the unactuated configuration,
a piercing member retainer connected to the piercing member,
the introducer member being configured to move relative to the connection hub from the unactuated configuration to an actuated configuration in which the introducer member pierces the first film, and
the piercing member being configured to telescope from the introducer member to move from the unactuated configuration to a delivery configuration in which the piercing tip is not disposed within the introducer member, the piercing member being adapted to pierce the pierceable seal in the delivery configuration, the piercing member providing a fluid pathway through the pierceable seal in the delivery configuration.

18. The assembly of claim 17 further comprising a second film, the pierceable seal forming a recess, the second film being coupled to the drug container over the recess, the introducer member piercing the first film and the second film in the actuated configuration.

19. A drug delivery pump comprising:
a housing;
an activation mechanism;
a drug container including a barrel, a cap, and a pierceable seal; and
a fluid pathway connection assembly including
a connection hub including an aperture,
a first film sealed along the aperture, the connection hub including a sterile cavity sealed by the first film,
an introducer member at least partially disposed within the sterile cavity in an unactuated configuration,
a piercing member configured to telescope from the introducer member, the piercing member including a piercing tip at least partially disposed within the introducer member in the unactuated configuration,
a piercing member retainer connected to the piercing member,
the introducer member being configured to move relative to the connection hub from the unactuated configuration to an actuated configuration in which the introducer member pierces the first film, and
the piercing member being configured to telescope from the introducer member to move from the unactuated configuration to a delivery configuration in which the piercing tip is not disposed within the introducer member, the piercing member being adapted to pierce the pierceable seal in the delivery configuration, the piercing member providing a fluid pathway through the pierceable seal in the delivery configuration.

20. The drug delivery pump of claim 19, further comprising a needle insertion mechanism, the needle insertion mechanism including a rotational biasing member configured to move at least one of the introducer member and the piercing member from the unactuated configuration to at least one of the actuated configuration and the delivery configuration.

* * * * *